(12) United States Patent
De Benedictis et al.

(10) Patent No.: US 11,020,421 B2
(45) Date of Patent: Jun. 1, 2021

(54) SUPERABSORBENT MATERIALS AND METHODS OF PRODUCTION THEREOF

(71) Applicant: GELESIS, LLC, Boston, MA (US)

(72) Inventors: Vincenzo Maria De Benedictis, San Vito Dei Normanni (IT); Christian Demitri, San Pietro In Lama (IT); Alessandro Sannino, Lecce (IT)

(73) Assignee: Gelesis LLC, Boston, MA (US)

( * ) Notice: Subject to any disclaimer, the term of this patent is extended or adjusted under 35 U.S.C. 154(b) by 0 days.

(21) Appl. No.: 15/944,960

(22) Filed: Apr. 4, 2018

(65) Prior Publication Data

US 2018/0289734 A1    Oct. 11, 2018

Related U.S. Application Data

(60) Provisional application No. 62/481,947, filed on Apr. 5, 2017.

(51) Int. Cl.

| | |
|---|---|
| *A61P 5/48* | (2006.01) |
| *A61P 3/04* | (2006.01) |
| *C08L 71/08* | (2006.01) |
| *C08L 1/28* | (2006.01) |
| *C08J 3/075* | (2006.01) |
| *C08J 3/24* | (2006.01) |
| *A61K 31/717* | (2006.01) |
| *A61K 47/10* | (2017.01) |
| *C08G 65/332* | (2006.01) |
| *C08L 71/02* | (2006.01) |
| *C08B 15/00* | (2006.01) |
| *C08B 37/00* | (2006.01) |
| *A61K 9/00* | (2006.01) |

(52) U.S. Cl.
CPC ............ *A61K 31/717* (2013.01); *A61K 47/10* (2013.01); *A61P 3/04* (2018.01); *A61P 5/48* (2018.01); *C08B 15/005* (2013.01); *C08B 37/0087* (2013.01); *C08G 65/3328* (2013.01); *C08J 3/075* (2013.01); *C08J 3/246* (2013.01); *C08L 1/286* (2013.01); *C08L 71/02* (2013.01); *C08L 71/08* (2013.01); *A61K 9/0095* (2013.01); *C08J 2301/10* (2013.01); *C08J 2305/00* (2013.01)

(58) Field of Classification Search
CPC .... A61K 9/0095; A61K 31/717; A61K 47/10; A61P 5/48; A61P 3/04; C08K 71/02; C08K 1/286; C08K 71/08; C08K 5/00; C08B 15/005; C08B 15/10; C08B 31/0087; A61L 15/00; A61L 15/18; A61L 15/42
USPC .................. 514/57; 523/105; 536/123.1, 124
See application file for complete search history.

(56) References Cited

U.S. PATENT DOCUMENTS

| | | | |
|---|---|---|---|
| 4,710,504 A * | 12/1987 | Baldwin | ............... C07D 471/20 514/210.02 |
| 5,550,189 A | 8/1996 | Qin et al. | |
| 6,703,444 B2 | 3/2004 | Zhao et al. | |
| 6,852,255 B2 | 2/2005 | Yang et al. | |
| 7,071,327 B2 * | 7/2006 | Mensitieri | ................ A61L 15/28 524/557 |
| 8,658,147 B2 | 2/2014 | Sannino et al. | |
| 9,161,987 B2 | 10/2015 | Falcone et al. | |
| 9,353,191 B2 | 5/2016 | Sannino et al. | |
| 9,855,294 B2 * | 1/2018 | Heshmati | .............. A61K 9/0095 |
| 10,086,014 B2 | 10/2018 | Sannino et al. | |
| 10,098,907 B2 * | 10/2018 | Sannino | ................. A61K 38/10 |
| 10,179,824 B2 * | 1/2019 | Sannino | ................ C08B 15/005 |
| 10,544,233 B2 | 1/2020 | Sannino et al. | |
| 10,584,183 B2 | 3/2020 | Sannino et al. | |
| 2003/0149263 A1 * | 8/2003 | Mensitieri | ............... A61L 15/28 536/120 |
| 2005/0281880 A1 | 12/2005 | Wang | |
| 2006/0142478 A1 | 6/2006 | Luo et al. | |
| 2008/0103228 A1 * | 5/2008 | Falcone | .................. A61F 2/441 523/105 |
| 2009/0214604 A1 | 8/2009 | Alvarez Lorenzo et al. | |
| 2010/0234233 A1 | 9/2010 | Sannino et al. | |
| 2013/0089737 A1 | 4/2013 | Sannino et al. | |
| 2015/0366898 A1 | 12/2015 | Heshmati et al. | |
| 2016/0222134 A1 | 8/2016 | Sannino et al. | |
| 2016/0319042 A1 | 11/2016 | Sannino et al. | |
| 2016/0361350 A1 | 12/2016 | Sannino et al. | |
| 2018/0153925 A1 | 6/2018 | Heshmati et al. | |
| 2019/0233545 A1 | 8/2019 | Sannino et al. | |

FOREIGN PATENT DOCUMENTS

| | | |
|---|---|---|
| EP | 1818344 | 8/2007 |
| EP | 1992364 A1 | 11/2008 |
| EP | 2236523 | 10/2010 |
| WO | 8600912 | 2/1986 |
| WO | 2012170682 A1 | 12/2012 |
| WO | 2018191752 A1 | 10/2018 |

OTHER PUBLICATIONS

Luo et al, Bioconjugate Chem., 1999, 10, 755-763.*
Kono, "Characterization and properties of carboxymethyl cellulose hydrogels crosslinked by polyethylene glycol," Carbohydrate Polymers, 106:84-93, 2014.

* cited by examiner

*Primary Examiner* — Ganapathy Krishnan
(74) *Attorney, Agent, or Firm* — Elmore Patent Law Group, P.C.; Carolyn Elmore; Edgar Harlan

(57) ABSTRACT

The present invention relates to new methods for crosslinking a polysaccharide with a bifunctional poly(ethylene glycol). The invention further includes the polymer hydrogels which can be produced using these methods, compositions comprising the polymer hydrogels and methods of use thereof.

11 Claims, 24 Drawing Sheets

SUPERABSORBENT MATERIALS AND METHODS OF PRODUCTION THEREOF

RELATED APPLICATION(S)

This application claims the benefit of U.S. Provisional Application No. 62/481,947, filed on Apr. 5, 2017. The entire teachings of the above application are incorporated herein by reference.

FIELD OF THE INVENTION

This invention relates to compositions of polymer hydrogels comprising polysaccharides cross-linked with bi- or polyfunctional polyethylene glycols (PEGs), a method for producing the hydrogels in the presence or absence of acid or base catalysis, and uses of the hydrogels as absorbent materials.

BACKGROUND OF THE INVENTION

Polymer hydrogels are cross-linked hydrophilic polymers that are capable of absorbing large amounts of water. In particular, cross-linked polymer hydrogels capable of absorbing an amount of water in excess of 10 times their dry weight are defined as "superabsorbent". Some of these materials are even capable of absorbing over 1 liter of water per gram of dry polymer (over 1000 times its dry weight).

The cross-links or cross-linking knots, i.e., the physical or chemical bonds between the macromolecular backbones forming the polymer hydrogel network, guarantee the structural integrity of the polymer-liquid system, on the one hand preventing the complete dissolution of the polymer, and on the other hand allowing the retention of the aqueous phase within the molecular mesh.

Some of the superabsorbent polymer hydrogels that are currently available on the market (i.e. HYSORB® and SAVIVA® from BASF, ZAPZORB® by ZappaTec, Accepta 4302 and 4303 from Accepta) are characterized not only by their marked absorption properties, but also by their biocompatibility, which is probably due to their high water content, and, above all, by the possibility of adjusting their absorption properties according to external stimuli. Consequently, such polymer hydrogels may be used as intelligent materials, for example for the manufacture of sensors or actuators for a number of industrial applications. Besides the usual applications as absorbent cores in the field of personal hygiene absorbent products, there are more recent and innovative applications such as in the biomedical field for the development of controlled release drug formulations, artificial muscles, sensors, etc., and in agriculture and horticulture, for example in devices for the controlled release of water and nutrients in arid soils.

However, the superabsorbent polymer hydrogels currently available are almost exclusively acrylic-based products, and hence not biodegradable.

Given the growing interest in environmental protection issues, over recent years interest has been focused on the development of superabsorbent materials based on biodegradable polymers having properties which are similar to those of the traditional superabsorbent polyacrylates. Examples of biodegradable polymers used to obtain superabsorbent polymer hydrogels include polysaccharides, such as starch, glucomannan, and cellulose derivatives.

There is a need for new biodegradable and biocompatible polymer hydrogels having desirable absorption and rheological properties.

SUMMARY OF THE INVENTION

The present invention relates to new methods for producing water-absorbent crosslinked polysaccharides. The present invention further includes the polymer hydrogels which can be produced using these methods, compositions comprising the polymer hydrogels and methods of use thereof.

In one embodiment, the invention provides a first method of producing a polymer hydrogel. The method comprises the steps of (1) producing an aqueous solution comprising one or more water-soluble polysaccharides and a polyfunctional polyethylene glycol; (2) drying the solution to produce a solid residue and (3) heating the solid residue, thereby producing the polymer hydrogel. The solution of step (1) preferably does not include an acid or base catalyst.

The invention further provides polymer hydrogels which can be prepared by the methods described herein, compositions comprising these polymer hydrogels and methods of using the polymer hydrogels.

DETAILED DESCRIPTION THE INVENTION

Figure 1:
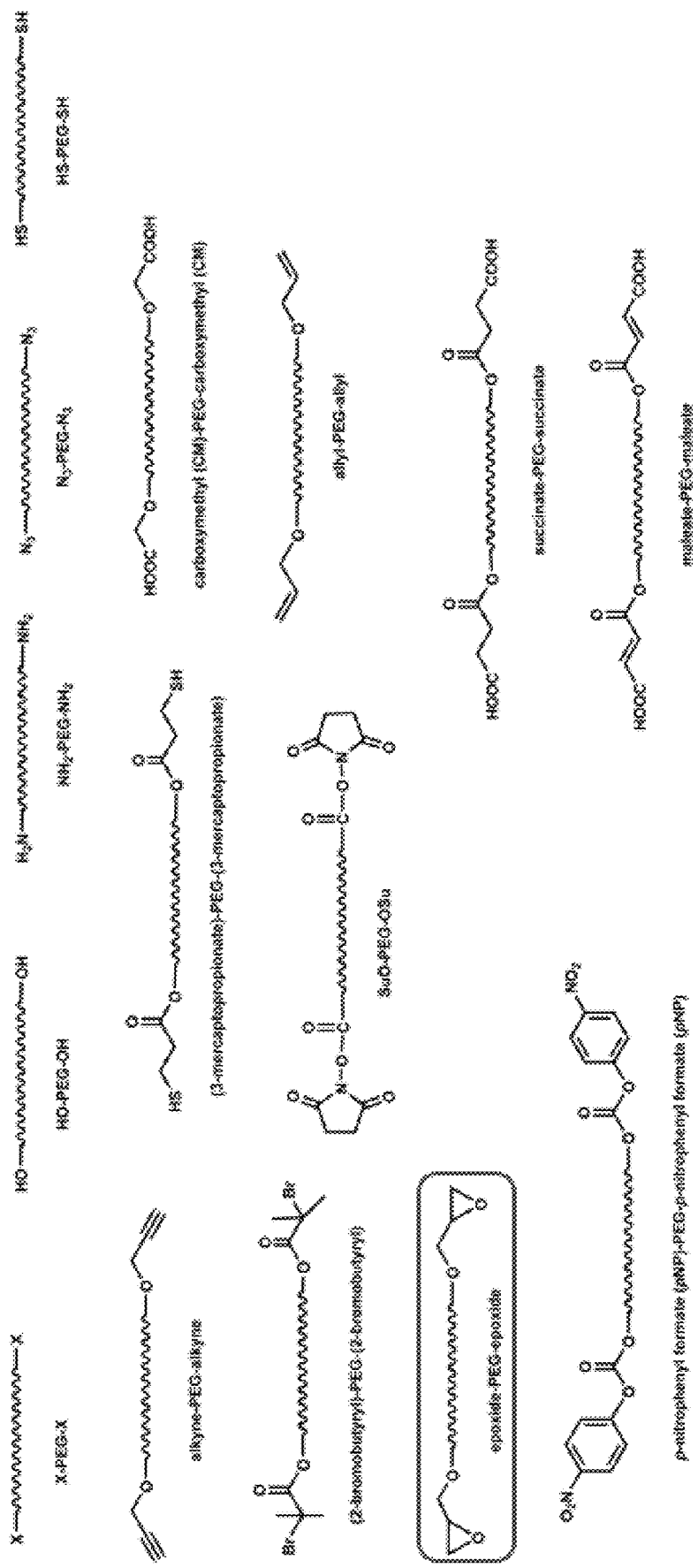
FIG. 1 illustrates exemplary bifunctional PEG crosslinking agents.

In one embodiment, the invention provides a first method of producing a polymer hydrogel comprising the steps of (1) preparing an aqueous solution of at least one water soluble polysaccharide and a bifunctional PEG; (2) drying the solution to produce a solid residue; and (3) heating the solid residue to produce the polymer hydrogel. Preferably, the solution of step (a) does not comprise an acid or base catalyst.

Preferably the total concentration of the water soluble polysaccharide in the aqueous solution is at least 0.5% by weight relative to water, preferably at least 2%, at least 3% or at least 4%. In certain embodiments, the total concentration of water soluble polysaccharide is 4-10% by weight, preferably 5-8% by weight, more preferably 5-7% by weight, 5.5-6.5% by weight or about 6% by weight.

The amount of bifunctional PEG in the aqueous solution of step (a) can be described in terms of either a weight ratio relative to the total weight of water soluble polymer in the solution or on a stoichiometric basis, i.e., the ratio of moles of the bifunctional PEG to moles of monomeric units of the water-soluble polysaccharide(s). In certain embodiments, the bifunctional PEG is present in the solution of step (a) in an amount such that the molar ratio of polysaccharide monomeric units to the bifunctional PEG is at least 100, preferably at least 200, more preferably from about 200 to about 30000. In certain embodiments, the molar ratio of polysaccharide monomers to bifunctional PEG is from 200 to 4000, 1000 to 3000, 1500 to 2500 or about 2500.

In certain embodiments, the weight ratio of bifunctional PEG to water soluble polysaccharide in the solution of step (a) is at least about 0.0005, preferably at least about 0.001. In certain embodiments, this weight ratio is from about 0.001 to about 0.1, preferably from about 0.005 to about 0.1, about 0.005 to about 0.05 or about 0.001 to about 0.1. In certain embodiments, this weight ratio is from about 0.005 to about 0.015 or about 0.01.

The solution of step (1) can be dried according to step (2) by evaporative drying, for example, at elevated temperature. Preferably, the solution is dried at a temperature of at least 25° C., at least 30° C., at least 40° C. or at least 50° C. Preferably, the solution is dried at a temperature less than 100° C. In certain embodiments, the solution is dried at a temperature from 30 to 70° C., from 35 to 65° C., from 40 to 60° C., from 45 to 55° C. or about 50° C. Preferably, the solution is dried to form a solid residue in the form of a film. Typically, the film retains some amount of water. For example, the film can be up to 30% water by weight, preferably up to 25%, 20%, 15% or 10% water by weight.

The solid residue is preferably heated in step (3) to a temperature of at least about 60° C. Preferably, the solid residue is heated to a temperature of at least about 70° C., 80° C., 90° C., 100° C. or 120° C. Preferably, the solid residue is heated to a temperature of about 90 to about 150° C., from about 95 to about 145° C., from about 100 to about 140° C., from about 110 to about 130° C. or about 120° C.

The solid residue is heated for a time sufficient to cross-link the water soluble polysaccharide with the bifunctional PEG. In certain embodiments, the residue is heated for at least 30 minutes. Preferably, the residue is heated for at least 1 hour. For example, the residue can be heated from 1 hour to 7 hours, 1.5 hours to 6.5 hours, 2 hours to 6 hours, 2.5 hours to 5.5 hours, 3 hours to 5 hours, 3.5 hours to 4.5 hours or about 4 hours.

In certain embodiments, the solid residue of step (2) is comminuted, for example, by grinding or milling, prior to heating according to step (3). The resulting particles preferably have a maximum cross-sectional diameter or greatest dimension within the range from about 5 micrometers to about 2,000 micrometers, preferably within the range from about 100 micrometers to about 1,000 micrometers. Preferably the average particle cross-sectional diameter is from about 300 micrometers to about 800 micrometers.

Polymer hydrogels produced according to methods of the invention can be further purified and/or dried. For example, the methods of the invention can further include the steps of purifying the polymer hydrogel, for example, by washing the polymer hydrogel in a polar solvent, such as water, a polar organic solvent, for example, an alcohol, such as methanol or ethanol, or a combination thereof. The polymer hydrogel immersed in the polar solvent swells and releases impurities, such as by-products or unreacted polyfunctional PEG. Water is preferred as the polar solvent, distilled and/or deionized water is still more preferred. The volume of water used in this step is preferably at least the volume to reach the maximum media uptake degree of the gel, or at least approximately 2- to 20-fold greater than the initial volume of the swollen gel itself. The polymer hydrogel washing step may be repeated more than once, optionally changing the polar solvent employed. For example, the polymer hydrogel can be washed with methanol or ethanol followed by distilled water, with these two steps optionally repeated one or more times.

The polymer hydrogel can further be dried to remove most or substantially all water.

In one embodiment, the drying step is carried out by immersing the fully swollen polymer hydrogel in a cellulose non-solvent, a process known as phase inversion. A "cellulose non-solvent", as this term is used herein, is a liquid compound which does not dissolve the water soluble polysaccharide and does not swell the polymer hydrogel, but is preferably miscible with water. Suitable cellulose non-solvents include, for example, acetone, methanol, ethanol, isopropanol and toluene. Drying the polymer hydrogel by phase inversion provides a final microporous structure which improves the absorption properties of the polymer hydrogel by capillarity. Moreover, if the porosity is interconnected or open, i.e. the micropores communicate with one another, the absorption/desorption kinetics of the gel will be improved as well. When a completely or partially swollen gel is immersed into a nonsolvent, the gel undergoes phase inversion with the expulsion of water, until the gel precipitates in the form of a vitreous solid as white coloured particles. Various rinses in the non-solvent may be necessary in order to obtain the dried gel in a short period of time. For example, when the swollen polymer hydrogel is immersed in acetone as the non-solvent, a water/acetone mixture is formed which increases in water content as the polymer hydrogel dries; at a certain acetone/water concentration, for example, about 55% in acetone, water is no longer able to exit from the polymer hydrogel, and thus fresh acetone has to be added to the polymer hydrogel to proceed with the drying process. Increasing the acetone/water ratio during drying increases the rate of drying. Pore dimensions are affected by the rate of the drying process and the initial dimensions of the polymer hydrogel particles: larger particles and a faster process tend to increase the pore dimensions; pore dimensions in the microscale range are preferred, as pores in this size range exhibit a strong capillary effect, resulting in the higher absorbency and water retention capacity.

In other embodiments, the polymer hydrogel is not dried by phase inversion. In these embodiments, the polymer hydrogel is dried by another process, such as air drying, vacuum drying, freeze drying or by drying at elevated temperature, for example, in an oven or vacuum oven. These drying methods can be used alone or in combination. In certain embodiments, these methods are used in combination with the non-solvent drying step described above. For example, the polymer hydrogel can be dried in a non-solvent, followed by air drying, freeze drying, oven drying, or a combination thereof to eliminate any residual traces of nonsolvent. Oven drying can be carried out at a temperature of, for example, approximately 30-45° C. until the water or residual non-solvent is completely removed. The washed and dried polymer hydrogel can then be used as is or can be milled to produce polymer hydrogel particles of a desired size.

The terms "bifunctional polyethylene glycol" and "bifunctional PEG" are used interchangeably herein and refer to a polyethylene glycol polymer which is functionalized at each end with a terminal reactive functional group. The polyethylene glycol polymer is preferably linear. Suitable reactive groups include those which are able to react with complementary groups in the polysaccharide, such as hydroxyl, carboxyl and amino groups, to form a covalent bond. Suitable such groups include azide, thiol, succinimide, epoxide, carboxy, amino, ethenyl, ethynyl, nitrophenyl, and bromoalkyl groups. Preferably, the functional group is stable in water at neutral pH. A preferred functional group is epoxide. Examples of suitable bifunctional PEGs include, but are not limited to, those set forth in FIG. 1.

The term "polyfunctional PEG" refers to a polyethylene glycol polymer which is functionalized with at least two reactive groups. Suitable polyfunctional PEGs include bifunctional PEGs as defined above, and PEGs having three or more reactive groups, particularly branched PEGs having three or more reactive groups, for example, a reactive functional group at the terminus of three or more arms of the branched PEG. Preferred polyfunctional PEGs include bifunctional PEGs and branched PEGs with 3 or 4 reactive groups. Bifunctional PEGs are particularly preferred.

The PEG unit of the bifunctional or polyfunctional PEG can be of any suitable length and is generally characterized by the number average molecular weight ($M_n$). In certain embodiments, the PEG has an $M_n$ from about 150 Da to about 20,000 Da, preferably from 200 Da to 10,000 Da, more preferably from 250 Da to 5000 Da, 400 Da to 2500 Da, 250 Da to 1000 Da, 350 Da to 650 Da, 450 Da to 550 Da or about 500 Da to about 550 Da. In certain embodiments, the PEG unit has an $M_n$ of about 400 Da to 7500 Da or about 500 Da to about 6500 Da. In certain embodiments, the PEG unit has an Mn of about 6000 Da.

Figure 2:
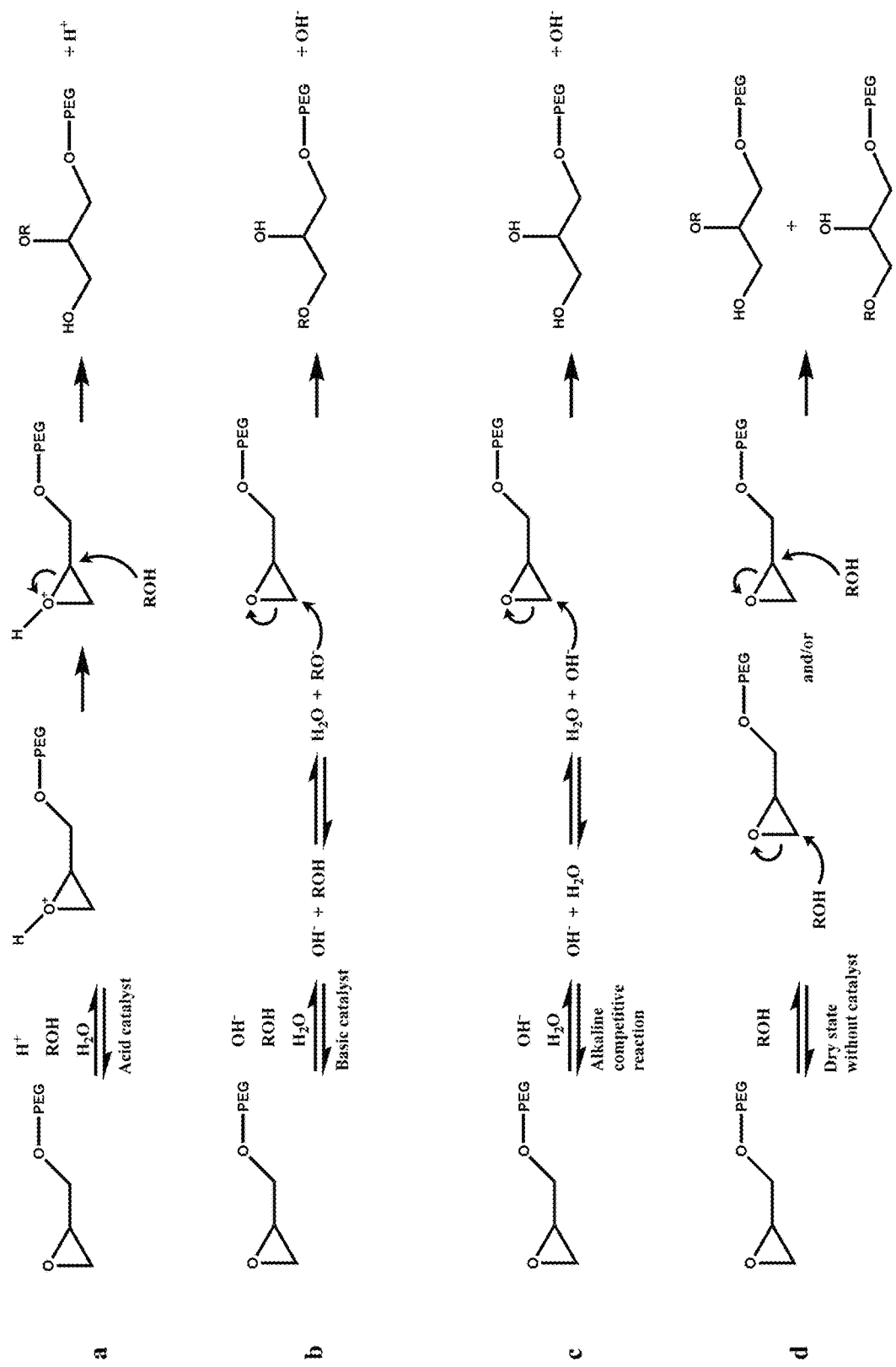
FIG. 2 illustrates the reactions that occur between an epoxide group of PEGDE and (a) a hydroxyl group of a polymer under acidic conditions; (b) a hydroxyl group of a polymer under basic conditions; (c) OH$^-$; and (d) a hydroxyl group of a polymer under dry conditions.

In preferred embodiments, the bifunctional PEG is that shown above as epoxide-PEG-epoxide, also referred to herein as PEG diglycidyl ether, PEG diepoxide or PEGDE. The epoxide moieties of PEGDE take part in several types of chemical reactions with functional groups of polysaccharides, such as the reactions summarized in FIGS. 2(a) to 2(d). FIG. 2(a) illustrates the reaction that occurs under acidic conditions, which generally involves two steps: 1. the epoxy oxygen atom is protonated; this step is rapid and the protonated and non-protonated forms exist in equilibrium. 2. Nucleophilic attack and addition of nucleophile ROH at a position that depends both on steric effects ($S_N1$) and substitution of carbon ($S_N2$); this step is slow and rate-determining. Under acidic conditions, both hydroxyl and carboxyl groups can react with epoxide; if the nucleophile is a hydroxyl group, an ether bond will be formed. If the nucleophile is the carboxylic/carboxylate group of the polymer, an ester bond will be formed. FIG. 2(b) shows the reaction mechanism under basic conditions. The strong nucleophile "RO$^-$" is formed by deprotonation of the precursor ROH by OH$^-$. Under these conditions, only the hydroxyl group reacts with the epoxide, and predominantly an ether bond will be formed. FIG. 2(c) illustrates a competitive side reaction that involves nucleophilic attack and addition of OH$^-$ itself instead of RO– with ring opening of epoxide, following the same mechanism of FIG. 2(b) ($S_N2$). This reaction wastes cross-linker without effective linking of the polysaccharide. This reaction is the reason that a higher amount of cross-linker is needed under basic conditions, compared with the amount needed in the dry process.

Figure 3:
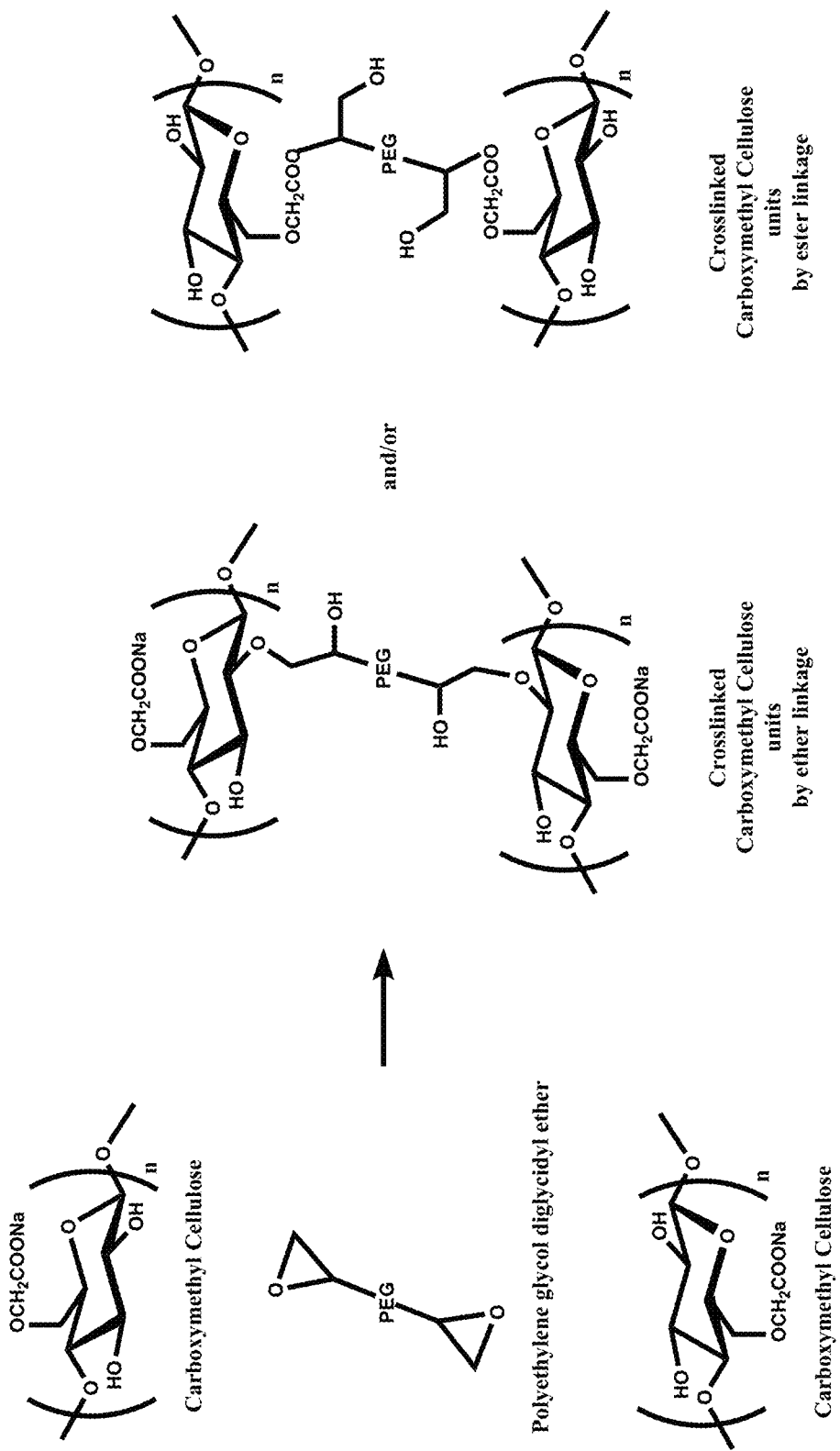
FIG. 3 illustrates the reaction between an epoxide group of PEGDE and a hydroxyl group of a polymer under dry conditions.
Figure 4:
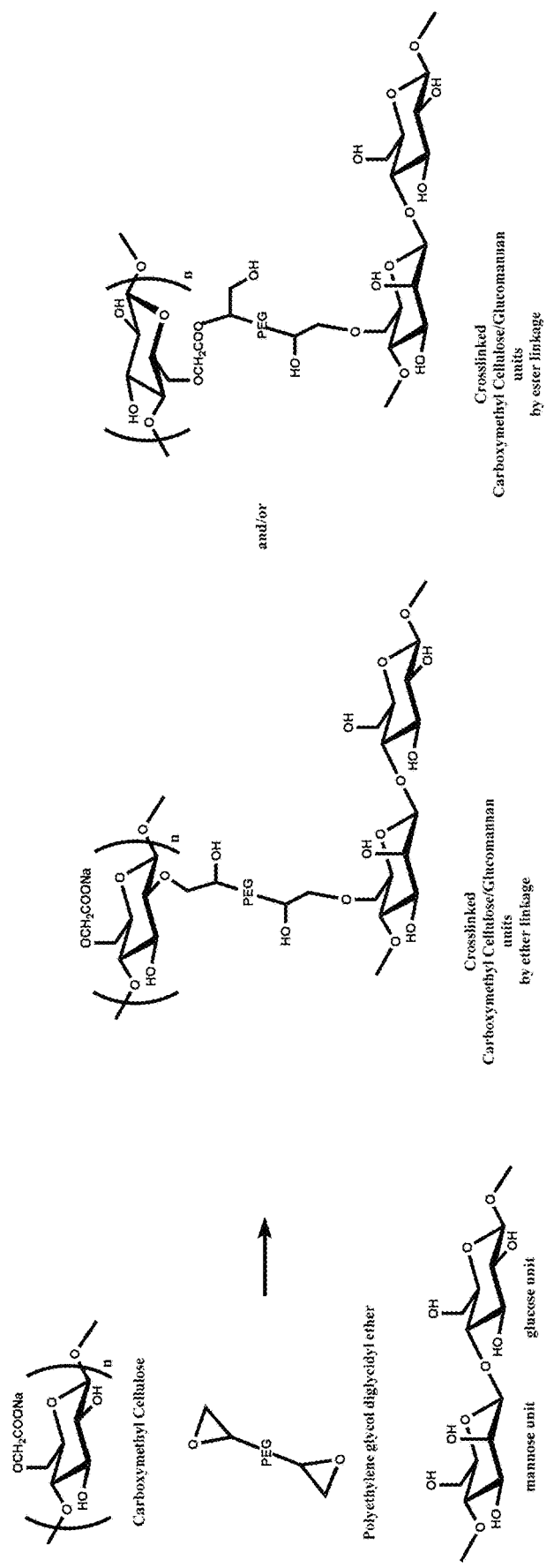
FIG. 4 illustrates the reaction between an epoxide group of PEGDE and a carboxyl group of a polymer under dry conditions.

FIG. 2(d) shows the reaction that occurs in the dry state in the absence of catalyst and involves nucleophilic attack and addition of nucleophile with ring opening of epoxide, in a position depending both on steric effects ($S_N1$) and substitution of carbon ($S_N2$). In this case, the only nucleophile that can react is ROH. This reaction is very slow in aqueous solution but is significant in the dry state. In fact, after drying, the nucleophilic substrate and epoxy ring are very close and are able to react, even when the epoxide group is present in low amounts. In the dry state with no catalyst, both hydroxyl and carboxyl groups can react with epoxide to form, respectively, an ether or an ester, as shown in FIGS. 3 and 4.

In certain embodiments of the methods of the invention, the bifunctional PEG is PEGDE having a molecular weight from about 450 to about 600 Da, or about 500 to about 550 Da or about 520 to about 530 Da. In certain embodiments of the methods of the invention, the bifunctional PEG is PEGDE having a molecular weight from about 400 to about 20000 Da, about 400 to about 10,000 Da, about 400 to about 7500 Da, about 500 to about 6500 Da or about 500 to about 6000 Da. In certain embodiments, the bifunctional PEG is such a PEGDE and the weight ratio of the water soluble polysaccharide(s) to PEGDE in the solution of step (1) is from about 20 to about 20000, preferably about 50 to about 10000 and more preferably about 100 to about 1000.

As used herein, the term "water soluble polysaccharide" refers to a polysaccharide or polysaccharide derivative which dissolves in water at a concentration of at least 4 weight %. Examples of suitable polysaccharides include substituted celluloses, substituted dextrans, substituted starches, glycosaminoglycans, chitosan, and alginates. Suitable polysaccharide derivatives include alkylcelluloses, such as $C_1$-$C_6$-alkylcelluloses, including methylcellulose, ethylcellulose and n-propylcellulose; hydroxyalkylcelluloses, including hydroxy-$C_1$-$C_6$-alkylcelluloses and hydroxy-$C_1$-$C_6$-alkyl-$C_1$-$C_6$-alkylcelluloses, such as hydroxyethylcellulose, hydroxy-n-propylcellulose, hydroxy-n-butylcellulose, hydroxypropylmethylcellulose, ethylhydroxyethylcellulose and carboxymethylcellulose; substituted starches, such as hydroxypropylstarch and carboxymethylstarch; substituted dextrans, such as dextran sulfate, dextran phosphate and diethylaminodextran; glycosaminoglycans, including heparin, hyaluronan, chondroitin, chondroitin sulfate and heparan sulfate; and polyuronic acids, such as polyglucuronic acid, polymanuronic acid, polygalacturonic acid and polyarabinic acid.

Preferably, at least one polysaccharide is an ionic polysaccharide. As used herein, the term "ionic polysaccharide" refers to a polymer comprising monomeric units having an acidic functional group, such as a carboxyl, sulfate, sulfonate, phosphate or phosphonate group, or a basic functional group, such as an amino, substituted amino or guanidyl group. When in aqueous solution at a suitable pH range, an ionic polysaccharide comprising acidic functional groups will be a polyanion, and such a polysaccharide is referred to herein as an "anionic polysaccharide". Likewise, in aqueous solution at a suitable pH range, an ionic polysaccharide comprising basic functional groups will be a polycation and is referred to herein as a "cationic polysaccharide". As used herein, the terms ionic polysaccharide, anionic polysaccharide and cationic polysaccharide refer to polysaccharides in which the acidic or basic functional groups are not charged, as well as polysaccharides in which some or all of the acidic or basic functional groups are charged, in combination with a suitable counterion. Suitable anionic polymers include alginate, dextran sulfate, carboxymethylcellulose, carboxymethylstarch, hyaluronic acid, polyglucuronic acid, polymanuronic acid, polygalacturonic acid, polyarabinic acid; chrondroitin sulfate and dextran phosphate. Suitable cationic polymers include chitosan and dimethylaminodextran. A preferred ionic polymer is carboxymethylcellulose, which can be used in the acid form, or as a salt with a suitable cation, such as sodium or potassium.

The term "non-ionic polysaccharide", as used herein, refers to a water soluble polysaccharide which does not comprise acidic or basic groups. Such a polysaccharide will be uncharged in aqueous solution. Examples of suitable non-ionic polysaccharides for use in the present methods are hydroxypropylstarch, mannans, glucomannan, acemannans, hydroxy-$C_1$-$C_6$-alkylcelluloses and hydroxy-$C_1$-$C_6$-alkyl-$C_1$-$C_6$-alkylcelluloses, such as hydroxyethylcellulose, hydroxy-n-propylcellulose, hydroxy-n-butylcellulose, hydroxypropylmethylcellulose, and ethylhydroxyethylcellulose.

In one embodiment, the water soluble polysaccharide of step (a) of the first embodiment or step (1) of the second embodiment is an ionic polysaccharide, preferably an anionic polysaccharide, and most preferably, carboxymethylcellulose.

In another embodiment, the water soluble polysaccharides of step (1) include an ionic polymer and a non-ionic polymer. The ionic polymer is preferably an anionic polymer, and most preferably, carboxymethylcellulose. The non-ionic polymer is preferably a natural dietary fiber, more preferably a resistant starch, glucomannan or hydroxyethylcellulose (HEC).

The weight ratios of the ionic and non-ionic polymers (ionic:non-ionic) can range from about 1:10 to about 10:1, preferably from about 1:5 to about 5:1. In preferred embodiments, the weight ratio is greater than 1:1, for example, from about 2 to about 5. In a particularly preferred embodiment, the ionic polymer is carboxymethycellulose, the non-ionic polymer is glucomannan, and the weight ratio (carboxymethylcellulose:glucomannan) is about 3:1.

The carboxymethylcellulose or salts thereof preferably have an average degree of substitution from about 0.3 to about 1.5, more preferably from about 0.4 to about 1.2. The degree of substitution refers to the average number of carboxyl groups present on the anhydroglucose unit of the cellulosic material. Carboxymethylcelluloses having an average degree of substitution within the range of from about 0.3 to about 1.5 are generally water-soluble. As used herein, a carboxymethylcellulose is considered to be "water-soluble" when it dissolves in water to form a true solution at a concentration of at least 2% by weight.

Carboxymethylcellulose is commercially available in a wide range of molecular weights. Carboxymethylcellulose having a relatively high molecular weight is preferred for use in the present invention. It is generally most convenient to express the molecular weight of a carboxymethylcellulose in terms of its viscosity in a 1.0 weight percent aqueous solution at 25° C. Carboxymethylcelluloses suitable for use in the present invention preferably have a viscosity in a 1.0 weight percent aqueous solution from about 50 centipoise to about 10,000 centipoise, more preferably from about 500 centipoise to about 10,000 centipoise, and most preferably from about 1,000 centipoise to about 2,800 centipoise. In one preferred embodiment, the carboxymethylcellulose has a weighted average molecular weight of 500 to 800 Kd.

In certain embodiments, the carboxymethylcellulose is a high viscosity carboxymethylcellulose. The term "high viscosity carboxymethylcellulose", as used herein, refers to carboxymethylcellulose, typically as the sodium salt, which forms a 1% (wt/wt) solution in water at 25 C having a viscosity of at least 6000 cps. The viscosity is determined according to the method set forth in Example 5 which is in accordance with ASTM D1439-03(2008)e1 (ASTM International, West Conshohocken, Pa. (2008), incorporated herein by reference in its entirety). In preferred embodiments, the high viscosity carboxymethylcellulose also has a low polydispersity index, such as a polydispersity index of about 8 or less.

In any embodiment of the invention, the high viscosity carboxymethylcellulose preferably forms a 1% (wt/wt) solution in water having a viscosity at 25° C. of at least about 6000, 7000, 7500, or 8000 cps. In certain embodiments, the carboxymethylcellulose forms a 1% (wt/wt) aqueous solution having a viscosity of 6000 to about 10000 cps or about 6000 to 11000 cps at 25° C. In certain embodiment, the carboxymethylcellulose forms a 1% (wt/wt) aqueous solution having a viscosity of about 6000 to about 9500 cps or about 7000 to 9500 cps at 25° C. In another embodiment, the carboxymethylcellulose forms a 1% (wt/wt) aqueous solution having a viscosity of about 7000 to about 9200 cps or about 7500 to 9000 cps at 25° C. In yet another embodiment, the carboxymethylcellulose forms a 1% (wt/wt) aqueous solution having a viscosity of about 8000 to about 9300 cps, or about 9000 cps at 25° C. Preferably the carboxymethylcellulose is in the form of the sodium salt. In preferred embodiments the carboxymethylcellulose is sodium carboxymethylcellulose which forms a 1% (wt/wt) aqueous solution having a viscosity of about 7800 cps or higher, for example, from about 7800 to 11000 cps, or about 8000 cps to about 11000 cps. In preferred embodiments, the high viscosity carboxymethylcellulose further has a polydispersity index (Mw/M') of about 8 or less, preferably about 7 or less, or 6 or less. In one embodiment, the polydispersity index is from about 3 to about 8, about 3 to about 7, about 3 to about 6.5, about 3.0 to about 6; about 3.5 to about 8, about 3.5 to about 7, about 3.5 to about 6.5, about 3.5 to about 6, about 4 to about 8, about 4 to about 7, about 4 to about 6.5, about 4 to about 6, about 4.5 to about 8, about 4.5 to about 7, about 4.5 to about 6.5, about 4.5 to about 6, about 5 to about 8, about 5 to about 7.5, about 5 to about 7, about 5 to about 6.5, or about 5 to about 6.

Suitable carboxymethylcelluloses are commercially available from numerous vendors. An example of a commercially available carboxymethylcellulose, are sodium carboxymethylcellulose products sold by Ashland/Aqualon Company under the trade designation AQUALON™, BLANOSE™ and BONDWELL™ depending on the geographical region in which it is sold. A suitable high viscosity carboxymethylcellulose sodium salt for use in the processes of the invention is AQUALON™ 7H4FM sold by Ashland Inc.

In a preferred embodiment of the method of the invention, which results in the formation of superabsorbent polymer hydrogels having a particularly high media uptake ratio (MUR), the total precursor concentration in the aqueous solution is of at least 2% by weight referred to the weight of the water of the starting aqueous solution, and the amount of the bifunctional PEG is from about 10% to about 0.05%, about 2% to about 0.05%, from about 1% to about 0.1% or from about 1.5% to about 0.05% by weight referred to the weight of the precursor. In the present description, the term "precursor" indicates the water soluble polysaccharide(s) used as the precursor for the formation of the polymer hydrogel polymer network. In certain embodiments, the "weight of the precursor" is the weight of CMCNa, when used alone, or the combined weights of CMCNa and glucomannan used.

The media uptake ratio (MUR) is a measure of the ability of the polymer hydrogel to absorb water or another specified aqueous solution. Unless otherwise noted, the term MUR relates to the uptake of distilled water. MUR is determined through equilibrium swelling measurements (using, for example, a Sartorius microscale with a sensitivity of $10^{-5}$ g) and it is calculated with the following formula:

$$MUR=(Ws-Wd)/Wd$$

wherein Ws is the weight of the polymer hydrogel after immersion in the aqueous solution, e.g., distilled water, after achieving equilibrium, and Wd is the weight of the dried polymer hydrogel before immersion.

Viscoelastic properties of the polymer hydrogels can be determined using equipment and methods known in the art. Small deformation oscillation measurements were carried out with a TA Rheometer, with plate-plate geometry. All measurements were performed with a gap of 4 mm with a peltier sensor at 25° C. The elastic modulus, G', and loss modulus, G", were obtained over a frequency range of 0.1-50 rad/sec.

One particularly preferred embodiment of the method of the invention comprises the following steps: Step 1, the hydrophilic polymer(s) and the PEGDE are dissolved in water at room temperature; Step 2, the water is removed from the solution at 40° C. over a two-day period, during this time cross-linking reaction spontaneously take place and a polymer hydrogel forms; Step 3, the product of Step 2 is optionally heated to 80° C. for 10 h to complete the cross-linking reaction; Step 4, the polymer hydrogel is washed three times with water over 24 h; Step 5, the washed polymer hydrogel is immersed in acetone for 24 h to remove water; Step 6, the polymer hydrogel is further dried in an oven at 45° C. for 5 h; and Step 7, the dried polymer hydrogel is milled to provide polymer hydrogel particles.

The polymer hydrogels of the invention have media uptake ratios in distilled water of at least about 10. Preferably, the polymer hydrogels of the invention are superabsorbent polymer hydrogels, for example, polymer hydrogels having an MUR of at least 10. In preferred embodiments, the polymer hydrogels of the invention have MURs at least about 20, about 30, about 40, about 50, about 60, about 70, about 80, about 90 or about 100. For example, in certain embodiments, the polymer hydrogels of the invention have MURs from about 10 to about 100, from about 20 to about 100, from about 30 to about 100, from about 40 to about 100, from about 50 to about 100, from about 60 to about 100, from about 70 to about 100, from about 80 to about 100, or from about 90 to about 100. In certain embodiments, the invention includes polymer hydrogels having MURs up to 150, 200, 250, 300, 330 or 350.

In certain embodiments, the polymer hydrogels of the invention can absorb an amount of one or more bodily fluids, such as blood, blood plasma, urine, intestinal fluid or gastric fluid, which is at least 10, 20, 30, 40, 50, 60, 70, 80, 90, or 100 times their dry weight. The ability of the polymer hydrogel to absorb bodily fluids can be tested using conventional means, including testing with samples of bodily fluids obtained from one or more subjects or with simulated bodily fluids, such as simulated urine or gastric fluid. In certain preferred embodiments, the polymer hydrogels can absorb significant amounts of a fluid prepared by combining one volume of simulated gastric fluid (SGF) with eight volumes of water. SGF can be prepared using USP Test Solutions procedures which are known in the art. In some embodiments, the polymer hydrogels of the invention have an MUR at least about 10, 20, 30, 40, 50, 60, 70, 80, 90, 100 or more in this SGF/water mixture.

The polymer hydrogels of the invention include cross-linked polymers having varying extents of hydration. For example, the polymer hydrogels can be provided in a state of hydration ranging from a substantially dry or anhydrous state, such as a state in which from about 0% to about 5% of the polymer hydrogel by weight is water or an aqueous fluid, to states comprising a substantial amount of water or aqueous fluid, including up to a state in which the polymer hydrogel has absorbed a maximum amount of water or an aqueous fluid.

In one embodiment, the present invention provides a pharmaceutical composition comprising a polymer hydrogel of the invention. The pharmaceutical composition can comprise the polymer hydrogel as an active agent, optionally in combination with a pharmaceutically acceptable excipient or carrier. For example, the pharmaceutical composition can be intended for oral administration to treat obesity, provide enhanced satiety, improve glycemic control, treat or prevent diabetes or aid in weight management. In another embodiment, the pharmaceutical composition comprises the polymer hydrogel in combination with another active agent. The polymer hydrogel can serve as a matrix, for example, for sustained release of the active agent.

The polymer hydrogels of the invention can be used in methods for treating overweight or obesity, reducing food or calorie intake or achieving or maintaining satiety. The methods comprise the step of administering an effective amount of a polymer hydrogel of the invention to the stomach of a subject, preferably by causing the subject, such as a mammal, including a human, to ingest the polymer hydrogel. Such polymer hydrogels can be used to take up stomach volume, for example, by increasing the volume of a food bolus without adding to the calorie content of the food. The polymer hydrogel can be ingested by the subject prior to eating or in combination with food, for example, as a mixture of the polymer hydrogel with food. Upon ingestion and contact with gastric fluid or a combination of gastric fluid and water, the polymer hydrogel will swell. The polymer hydrogel can be ingested alone or in a mixture with liquid or dry food in a dry, partially swollen or fully swollen state, but is preferably ingested in a state of hydration which is significantly below its fluid capacity, more preferably the polymer hydrogel is ingested in an anhydrous state. Thus, the volume of the stomach taken up by the polymer hydrogel can be significantly greater than the volume of the polymer hydrogel ingested by the subject. The polymer hydrogels of the invention can also take up volume and/or exert pressure on the wall of the small intestine by moving from the stomach into the small intestine and swelling. Preferably, the polymer hydrogel will remain swollen in the small intestine for a period of time sufficient to inhibit the intake of food by the subject, before shrinking in the colon sufficiently for excretion from the body. The time sufficient to inhibit the intake of food by the subject will generally be the time required for the subject to eat and for the ingested food to pass through the small intestine. Such shrinking can occur, for example, by degradation through loss of cross-links, releasing fluid and decreasing in volume sufficiently for excretion from the body. Preferred polymers for use in this method exhibit pH-dependent swelling, with greater swelling observed at higher pH than at lower pH. Thus, such a polymer will not swell significantly in the stomach unless food and/or water is present to raise the pH of the stomach contents and will move into the small intestine. When ingested with food, the polymer hydrogel will initially swell in the stomach, shrink when the stomach pH drops, and then move from the stomach to the small intestine. In the higher pH environment of the small intestine the polymer hydrogel will swell, taking up volume in the small intestine and/or exerting pressure on the wall of the small intestine.

The present polymer hydrogels can also be used for removing water from the gastrointestinal tract, for example, as a treatment for subjects suffering from kidney disease, including chronic and acute kidney disease, particularly subjects undergoing kidney dialysis. The polymer hydrogels can further be used to modify the fluid content (such as delivering water to the colon) in the gastrointestinal tract of a subject in need thereof, for example, for the treatment of constipation.

The polymer hydrogel of the invention can be administered to the subject in the form of a tablet or a capsule or other formulation suitable for oral administration. The tablet or capsule can optionally further include one or more additional agents, such as a pH modifying agent, and/or a pharmaceutically acceptable carrier or excipient. The polymer hydrogel can also be administered as a component of a food or a beverage, such as is described in WO 2010/059725, incorporated herein by reference in its entirety.

The invention further includes articles of manufacture which comprise the polymer hydrogels of the invention. Such articles of manufacture include articles in which polyacrylic polymer hydrogels are conventionally used, in consumer products, such as for example absorbent products for personal care (i.e., diapers, sanitary towels, etc.) and in products for agriculture (e.g., devices for the controlled release of water and nutrients). The absorption properties of the polymer hydrogels of the invention, which in some embodiments depend on the amount of carboxymethylcellulose employed and which can be improved by the induction of a microporosity in the gel structure, are comparable to those of polyacrylic gels. The polymer hydrogels obtainable by the method of the present invention therefore possess mechanical properties which make them suitable for use in all of the above-mentioned fields. The present polymer hydrogels, however, have advantages over acrylic polymer hydrogels, such as biodegradability, the absence of any toxic by-products during the manufacturing process and the use of fewer and readily available reagents. Such features enable a real employment of the polymer hydrogels of the invention in the biomedical and pharmaceutical fields as well.

Thus, the scope of the present invention also includes the use of the polymer hydrogels obtainable by the method of the invention as an absorbent material in products which are capable of absorbing water and/or aqueous solutions and/or which are capable of swelling when brought into contact with water and/or an aqueous solution.

EXAMPLES

The materials and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, derivatives, formulations and/or methods of the invention may be made without departing from the spirit of the invention and the scope of the appended claims.

Materials

SODIUM Carboxymethylcellulose (NaCMC)—
AQUALON™ 7H3 sodium carboxymethylcellulose—average degree of substitution of about 0.89 and a viscosity in a 1 percent aqueous solution at 25° C. of about 1000-3000 centipoise.

AQUALON™ 7H4 sodium carboxymethylcellulose-average degree of substitution of about 0.74 and a viscosity in a 1 percent aqueous solution at 25° C. of about 6000-12000 centipoise.

Glucomannan (GMN)—viscosity in a 1 percent aqueous solution at 25° C. of about 30,000 centipoise.

Polyethylene glycol diglycidyl ether, Mn=526 Da ($PEGDE_{500}$)-Sigma Aldrich.

Polyethylene glycol diglycidyl ether, Mn=6000 Da ($PEGDE_{6000}$)-Sigma Aldrich.

Sodium hydroxide-Sigma Aldrich

Method for Crosslinking of Sodium Carboxymethylcellulose with Catalyst

NaCMC was dissolved in distilled water to form a stock solution containing from 6 to 10 percent NaCMC by weight based on total solution weight (Solution A). PEGDE$_{500}$ was dissolved in water to form a stock solution containing 1 percent PEGDE$_{500}$ by weight based on total solution weight (Solution B). Sodium hydroxide was dissolved in water to form a stock solution containing 4 percent NaOH (1M) by weight based on total solution weight (Solution C). Solution B is then added to Solution A to provide a solution with the desired ratio of NaCMC and PEGDE. An amount of solution C is added to the solution of NaCMC and PEGDE$_{500}$ to yield a hydroxide concentration in the final solution of 0.25M. The resulting solution consisting of NaCMC, PEGDE$_{500}$ and NaOH is then thoroughly mixed. The homogenous mixture is then cast by evaporative drying at 50° C. in an air-convection oven. After drying, the recovered cross-linked carboxymethylcellulose was ground into granules in a blender. In certain cases, the cross-linked carboxymethylcellulose was then treated at 120° C. from 2 to 20 hours in an oven to complete cross-linking reaction. In certain cases, the cross-linked carboxymethylcellulose was washed with acidic water (0.25M hydrochloric acid) from 1 to 3 hours to remove unreacted materials and byproducts and to neutralize catalyst.

Method for Crosslinking of Sodium Carboxymethylcellulose without Catalyst

NaCMC was dissolved in distilled water to form a stock solution containing from 6 to 10 percent NaCMC by weight based on total solution weight (Solution A). PEGDE$_{500}$ or PEGDE$_{6000}$ was dissolved in water to form a stock solution containing 1 percent PEGDE by weight based on total solution weight (Solution B). Solution B is then added to Solution A to provide a solution with the desired ratio of NaCMC and PEGDE. The resulting solution consisting of NaCMC and PEGDE is then thoroughly mixed. The homogenous mixture is then cast by evaporative drying at 50° C. in an air-convection oven. After drying, the recovered cross-linked carboxymethylcellulose was ground into granules in a blender. In certain cases, the cross-linked carboxymethylcellulose was then treated at 120° C. from 2 to 20 hours in an oven to complete cross-linking reaction. In certain cases, the cross-linked carboxymethylcellulose was washed with distilled water from 1 to 3 hours to remove unreacted materials and byproducts.

Method for Crosslinking of Mixtures of Sodium Carboxymethylcellulose and Glucomannan with Catalyst Each NaCMC was individually mixed with glucomannan as a powder state and the powder mixture was dissolved in distilled water to form a solution containing from 6 to 10 percent weight of NaCMC/glucomannan blend based on total solution weight (Solution A1). PEGDE was dissolved in water to form a solution containing 1 percent weight of PEGDE$_{500}$ based on total solution weight (Solution B). Sodium hydroxide was dissolved in water to form a solution containing 4 percent weight NaOH (1M) based on total solution weight (Solution C). Solution B was then added to Solution A1 to provide various concentrations of PEGDE$_{500}$ based on total weight of the NaCMC/glucomannan blend present in the aqueous solution. Solution C was then added to the solution containing the NaCMC/glucomannan blend and PEGDE$_{500}$ to provide a hydroxide concentration of 0.25M in the final solution. Each of the resulting solutions was then thoroughly mixed. The homogenous mixture was then cast by evaporative drying at 50° C. in an air-convection oven. After drying, the recovered cross-linked NaCMC/glucomannan blend was ground into granules in a blender. In certain case the cross-linked NaCMC/glucomannan blend was heated at 120° C. for from 2 to 20 hours in an oven to complete cross-linking reaction. In certain cases, the cross-linked NaCMC/glucomannan blend was washed was washed with acidic water (0.25M hydrochloric acid) from 1 to 3 hours to remove unreacted materials and byproducts and to neutralize catalyst.

Method for Crosslinking of Mixtures of Sodium Carboxymethylcellulose and Glucomannan without Catalyst Each NaCMC was individually mixed with glucomannan as a powder state and the powder mixture was dissolved in distilled water to form a solution containing from 6 to 10 percent weight of NaCMC/glucomannan blend based on total solution weight (Solution A1). PEGDE was dissolved in water to form a solution containing 1 percent weight of PEGDE based on total solution weight (Solution B). Solution B was then added to Solution A1 to provide various concentrations of PEGDE based on total weight of the NaCMC/glucomannan blend present in the aqueous solution. Each of the resulting solutions was then thoroughly mixed. The homogenous mixture was then cast by evaporative drying at 50° C. in an air-convection oven. After drying, the recovered cross-linked NaCMC/glucomannan blend was ground into granules in a blender. In certain case the cross-linked NaCMC/glucomannan blend was heated at 120° C. for from 2 to 20 hours in an oven to complete cross-linking reaction. In certain cases, the cross-linked NaCMC/glucomannan blend was washed was washed with distilled water from 1 to 3 hours to remove unreacted materials and byproducts.

Evaluation of Absorbency Properties of Polymer Hydrogels

The absorbency properties of polymer hydrogels obtained in certain of the previous examples were studied in various media at 37° C. The dried polymer hydrogel (100 mg) was immersed in either SGF or SGF/water 1:8 and allowed to swell until equilibrium was reached. The swelling ratio in each medium was measured at various time points.

To simulate the effect of digestion on a hydrated polymer hydrogel, to the polymer hydrogel swollen in SGF/water 1:8 for 60 minutes, 100% SGF was slowly added to collapse the gel particles. The MUR was monitored at various time points. Experiments were conducted by monitoring the MUR through a full cycle of swelling in 1:8 SGF/water, de-swelling in SGF/water 1:4, collapsing in SGF, re-swelling in simulated intestinal fluid (SIF), and degradation in simulated colonic fluid (SCF), all at 37° C.

Characterization of Crosslinked Materials

Unless otherwise noted, the measurements described below are made using samples of crosslinked materials with the following characteristics 1) a loss on drying of 10% or less; and (2) in the form of particulates which are at least 95% by mass in the size range of 100 μm to 1000 μm with an average size in the range of 400 to 800 µm. Certain of the methods below describe the use of specific instruments. In each case, an equivalent instrument can be used as is known in the art.

(A) Determination of Loss on Drying

The moisture content of a crosslinked material is determined according to USP <731>, Loss on Drying.

Instruments/Equipment

Moisture Analyzer Radwag, Model WPS 505
Lab Spatula
Aluminum crucible
Desiccator with silica gel Procedure 1. Place the sample in the desiccator for at least 12 hours.
2. Place the aluminum crucible on the scale pan of the moisture analyzer and tare the balance.
3. Accurately weigh 1.000±0.005 g of a sample in the aluminum crucible. The initial weight of the sample is $W_i$.
4. Set the moisture analyzer to heat the sample at 105° C. for 30 minutes under ambient pressure and moisture.
5. Turn on the Moisture Analyzer and run the LOD program (30 min at 105° C.).
6. Weigh the sample. The final weight of the sample is $W_f$. The LOD value is determined according to the equation:

$$LOD=(W_i-W_f)/W_i \times 100\%.$$

The Loss on Drying is determined in triplicate, and the reported LOD is the average of the three values.

(B) Determination of Particle Size Range

Equipment and Materials:
Sieve Shaker Retsch, Model AS 200 basic
Stainless Steel Sieves with mesh sizes 1000 µm and 100 µm
Aluminum weighing pan
Laboratory stainless steel spatula
Calibrated balance, capable of weighing to the nearest 0.1 g Procedure 1. Weigh the empty sieves and the aluminum pan to the nearest 0.1 g.
2. Weigh out 40.0±0.1 g of powder.
3. Stack the test sieves with sizes 1000 and 100 µm with larger pore size on the top and the smaller at the bottom. Assemble the aluminum pan at the bottom of the nest.
4. Pour the sample into the 1000 µm sieve, at the top of the stack.
5. Place this stack between the cover and the end pan of the shaker, so that the sample remains in the assembly.
6. Turn on the main switch of the shaker.
7. Set knob UV2 of the shaker for continuous operation.
8. Turn the knob MN2 of the shaker to the right to increase the vibration height until 50.
9. Shake this stack with the shaker for 5 minutes.
10. Disassemble the sieve and reweigh each sieve.
11. Determine the percentage weight of test specimen in each sieve as described in paragraph 8.
12. After measuring the weight of the full and empty test sieves, determine, by difference, the weight of the material inside each sieve.
13. Determine the weight of material in the collecting pan in a similar manner.
14. Use the weight of sample contained in each sieve and in the collecting pan to calculate the % distribution with the following equation:

$$Wx\% = Wx/W\text{sample} * 100\%$$

where:
Wx %=sample weight in each sieve or in the collecting pan, in percentage where the index "x" is:
">1000" for particle size bigger than 1000
"100-1000" for particle size between 100 and 1000
"<100" for particle size smaller than 100
Wsample=initial weight of test specimen.

(C) Determination of Tapped Density

Equipment and materials:
100 mL glass graduated cylinder
100 mL glass beaker
Lab spatula
Mechanical tapped density tester, Model JV 1000 by Copley Scientific
Calibrated balance capable of weighing to the nearest 0.1 g.

Procedure

1. Weigh out 40.0±0.1 grams of test sample. This value is designated M.
2. Introduce the sample into a dry 100 mL glass graduated cylinder.
3. Carefully level the powder without compacting and read the unsettled apparent volume, V0, to the nearest graduated unit.
4. Set the mechanical tapped density tester to tap the cylinder 500 times initially and measure the tapped volume, V500, to the nearest graduated unit.
5. Repeat the tapping 750 times and measure the tapped volume, V750, to the nearest graduated unit.
6. If the difference between the two volumes is less than 2%, V750 is the final tapped volume, Vf, otherwise repeat in increments of 1250 taps, as needed, until the difference between succeeding measurements is less than 2%.

Calculations

Calculate the Tapped Density, DT, in gram per mL, by the formula:

$$DT=M/Vf$$

where:
M=Weight of sample, in grams, rounded off to the nearest 0.1 g.
Vf=Final volume, in mL.

(D) Determination of Media Uptake Ratio in SGF/Water (1:8)

The media uptake ratio of a crosslinked materials in SGF/water (1:8) is determined according to the following protocol.
1. Place a dried fritted glass funnel on a support and pour 40.0±1.0 g of purified water into the funnel.

2. Wait until no droplets are detected in the neck of the funnel (about 5 minutes) and dry the tip of the funnel with an absorbent paper.

3. Place the funnel into an empty and dry glass beaker (beaker #1), place them on a tared scale and record the weight of the empty apparatus ($W_{tare}$).

4. Put a magnetic stir bar in a 100 mL beaker (beaker #2); place beaker #2 on the scale and tare.

5. Add 40.0±1.0 g of SGF/Water (1:8) solution prepared as described above to beaker #2.

6. Place beaker #2 on the magnetic stirrer and stir gently at room temperature.

7. Accurately weigh 0.250±0.005 g of crosslinked material powder using a weighing paper ($W_{in}$).

8. Add the powder to beaker #2 and stir gently for 30±2 min with the magnetic stirrer without generating vortices.

9. Remove the stir bar from the resulting suspension, place the funnel on a support and pour the suspension into the funnel, collecting any remaining material with a spatula.

10. Allow the material to drain for 10±1 min.

11. Place the funnel containing the drained material inside beaker #1 and weigh it ($W'_{fin}$).

The Media Uptake Ratio (MUR) is calculated according to $$MUR = (W_{fin} - W_{in})/W_{in}.$$

$W_{fin}$ is the weight of the swollen hydrogel calculated as follows $$W_{fin} = W'_{fin} - W_{tare}$$

$W_{in}$ is the weight of the initial dry sample.

The MUR is determined in triplicate for each sample of crosslinked material and the reported MUR is the average of the three determinations.

(E) Determination of Elastic Modulus

The elastic modulus (G') is determined according to the protocol set forth below. The rheometer used is a Rheometer Discovery HR-1 (5332-0277 DHR-1) by TA Instruments or equivalent, equipped with a Peltier Plate; a Lower Flat plate Xhatch, 40 mm diameter; and an Upper Flat plate Xhatch, 40 mm diameter.

1. Put a magnetic stir bar in a 100 mL beaker.

2. Add 40.0±1.0 g of SGF/Water (1:8) solution prepared as described above to the beaker.

3. Place the beaker on the magnetic stirrer and stir gently at room temperature.

4. Accurately weigh 0.250±0.005 g of crosslinked material powder using a weighing paper ($W_{in}$).

5. Add the powder to the beaker and stir gently for 30±2 min with the magnetic stirrer without generating vortices.

6. Remove the stir bar from the resulting suspension, place the funnel on a support and pour the suspension into the funnel, collecting any remaining material with a spatula.

7. Allow the material to drain for 10±1 min.

8. Collect the resulting material.

9. Subject the material to a sweep frequency test with the rheometer and determine the value at an angular frequency of 10 rad/s.

The determination is made in triplicate. The reported G' value is the average of the three determinations.

Results

The parameters for a series of reactions and the MUR and G' results in 1:8 SGF/water for each product are shown in the table below. The crosslinker in reactions 1-44 is $PEGDE_{500}$. The crosslinker in reactions 45-52 is $PEGDE_{6000}$.

| Reaction | Polymer | $PEGDE_{500}$/polymer Ratio (g/g) | Catalyst NaOH 0.25M | Thermal treatment: time (h) | Thermal treatment: temp (° C.) | Washing time (h) | MUR (in 1:8 $SGF:H_2O$) | Storage modulus G' (Pa) (in 1:8 $SGF:H_2O$) |
|---|---|---|---|---|---|---|---|---|
| 1 | 7H3 | 0 (control) | Yes | none | none | none | dissolved | none |
| 2 | 7H3 | 0 (control) | No | none | none | none | dissolved | none |
| 3 | 7H3 | 0 (control) | Yes | 4 h | 120° C. | 1 h | dissolved | none |
| 4 | 7H3 | 0 (control) | No | 4 h | 120° C. | 1 h | dissolved | none |
| 5 | 7H3 | 0.01 | Yes | none | none | none | 85 | none |
| 6 | 7H3 | 0.01 | Yes | 4 h | 120° C. | none | dissolved | none |
| 7 | 7H3 | 0.01 | Yes | none | none | 1 h | dissolved | none |
| 8 | 7H3 | 0.01 | No | none | none | none | 71 | 680 |
| 9 | 7H3 | 0.01 | No | none | none | 1 h | 80 | 22 |
| 10 | 7H3 | 0.01 | No | none | none | 3 h | 89 | 10 |
| 11 | 7H3 | 0.01 | No | 4 h | 120° C. | none | 50 | 1550 |
| 12 | 7H3 | 0.01 | No | 4 h | 120° C. | 1 h | 69 | 941 |
| 13 | 7H3 | 0.001 | Yes | none | none | none | dissolved | none |
| 14 | 7H3 | 0.001 | Yes | 4 h | 120° C. | none | dissolved | none |
| 15 | 7H3 | 0.001 | No | none | none | none | 84 | 172 |
| 16 | 7H3 | 0.001 | No | 4 h | 120° C. | none | 72 | 940 |
| 17 | 7H4 | 0 (control) | Yes | none | none | none | dissolved | none |
| 18 | 7H4 | 0 (control) | No | none | none | none | dissolved | none |
| 19 | 7H4 | 0 (control) | Yes | 4 h | 120° C. | none | dissolved | none |
| 20 | 7H4 | 0 (control) | No | 4 h | 120° C. | none | dissolved | none |
| 21 | 7H4 | 0.001 | Yes | none | none | none | 51 | 180 |
| 22 | 7H4 | 0.001 | No | none | none | none | 42 | 2250 |
| 23 | 7H4 | 0.001 | No | none | none | 1 h | 108 | 798 |
| 24 | 7H4 | 0.001 | No | none | none | 3 h | 93 | 791 |
| 25 | 7H4 | 0.001 | No | 4 h | 120° C. | none | 32 | 4490 |
| 26 | 7H4 | 0.001 | No | 4 h | 120° C. | 1 h | 64 | 2316 |
| 27 | 7H4 | 0.0001 | Yes | none | none | none | 55 | 120 |
| 28 | 7H4 | 0.0001 | No | none | none | none | 71 | 442 |
| 29 | 7H4 | 0.0001 | No | 4 h | 120° C. | none | 36 | 3500 |
| 30 | 7H3/GMN (75:25) | 0 (control) | Yes | none | none | none | dissolved | none |

| | | | | | | | | |
|---|---|---|---|---|---|---|---|---|
| 31 | 7H3/GMN (75:25) | 0 (control) | No | none | none | none | dissolved | none |
| 32 | 7H3/GMN (75:25) | 0.001 | No | none | none | none | 28 | 378 |
| 33 | 7H3/GMN (75:25) | 0.001 | No | 4 h | 120° C. | none | 19 | 1510 |
| 34 | 7H4/GMN (75:25) | 0 (control) | Yes | none | none | none | dissolved | none |
| 35 | 7H4/GMN (75:25) | 0 (control) | No | none | none | 1 h | dissolved | none |
| 36 | 7H4/GMN (75:25) | 0.001 | No | none | none | none | 40 | 2074 |
| 37 | 7H4/GMN (75:25) | 0.001 | No | 4 h | 120° C. | none | 16 | 5671 |
| 38 | 7H4/GMN (75:25) | 0.001 | No | none | none | 1 h | dissolved | none |
| 39 | 7H4/GMN (75:25) | 0.001 | No | none | none | 3 h | dissolved | None |
| 40 | 7H4/GMN (75:25) | 0.001 | No | 4 h | 120° C. | 1 h | 40 | 5000 |
| 41 | 7H3/GMN (90:10) | No | none | none | none | none | 65 | 1089 |
| 42 | 7H3/GMN (90:10) | No | 4 h | 120° C. | none | none | 33 | 2825 |
| 43 | 7H3/GMN (50:50) | No | none | none | none | none | 6 | 2481 |
| 44 | 7H3/GMN (50:50) | No | 4 h | 120° C. | none | none | 18 | 6540 |

| Reaction | Polymer | PEGDE$_{6000}$/ polymer Ratio (g/g) | Catalyst NaOH 0.25M | Thermal treatment: time (h) | Thermal treatment: temp (° C.) | Washing time (h) | MUR (in 1:8 SGF:H$_2$O) | Storage modulus G' (Pa) (in 1:8 SGF:H$_2$O) |
|---|---|---|---|---|---|---|---|---|
| 45 | 7H3 | 0.01 | No | none | none | none | dissolved | none |
| 46 | 7H3 | 0.01 | No | 4 h | 120° C. | none | 91 | 495 |
| 47 | 7H3 | 0.001 | No | none | none | none | dissolved | none |
| 48 | 7H3 | 0.001 | No | 4 h | 120° C. | none | 100 | 355 |
| 49 | 7H4 | 0.01 | No | none | none | none | dissolved | none |
| 50 | 7H4 | 0.01 | No | 4 h | 120° C. | none | 32 | 4300 |
| 51 | 7H4 | 0.001 | No | none | none | none | dissolved | none |
| 52 | 7H4 | 0.001 | No | 4 h | 120° C. | none | 36 | 3200 |

The properties of selected hydrogels under simulated digestion conditions are shown in FIGS. 5-24.

Figure 5:
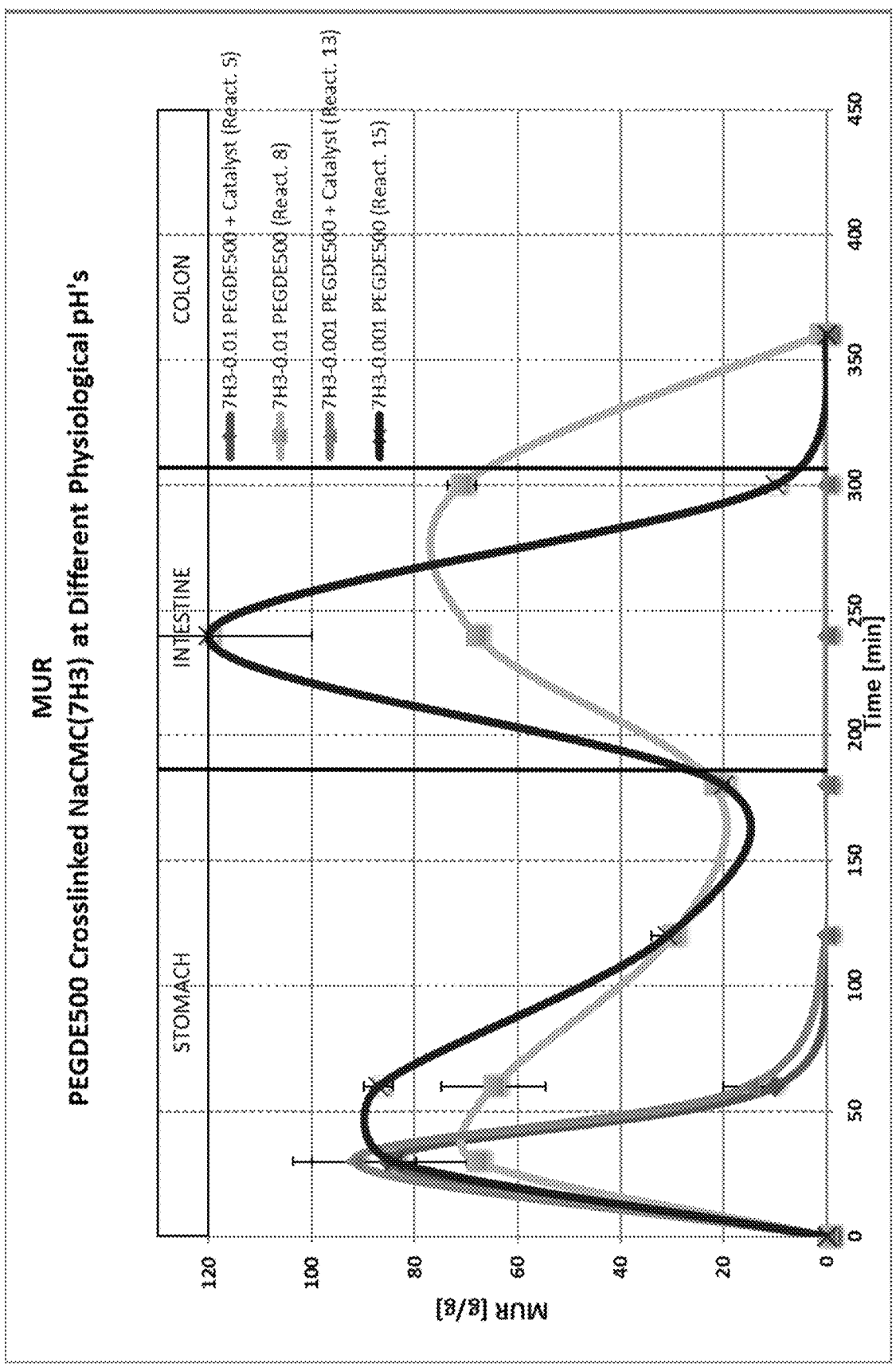
FIG. 5 is a graph of MUR vs. time and simulated physiological conditions for hydrogels produced from 1 g of 7H3 NaCMC and either 0.01 or 0.001 g of PEGDE$_{500}$ without heat treatment and both with and without catalyst.
Figure 6:
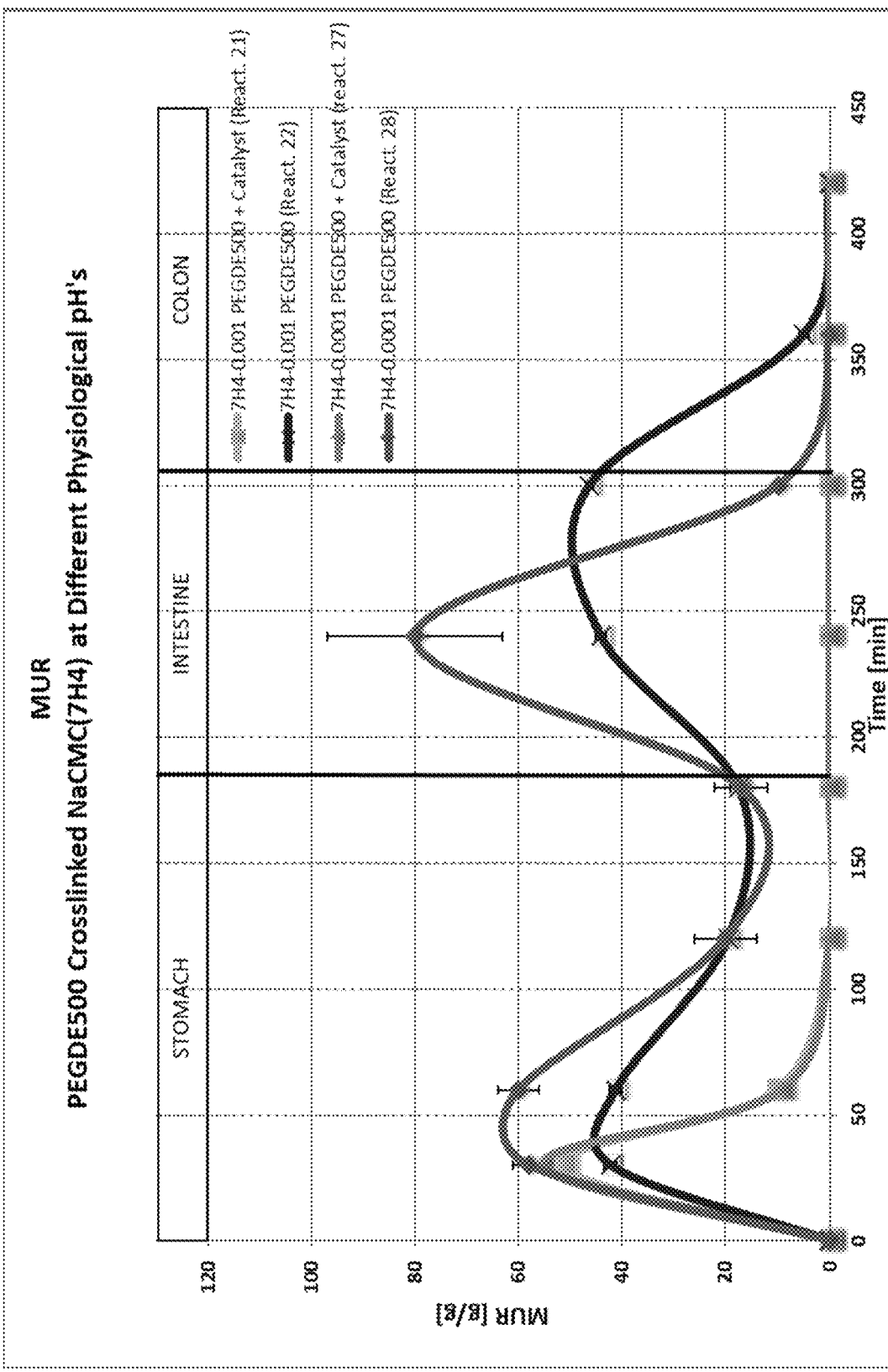
FIG. 6 is a graph of MUR vs. time and simulated physiological conditions for hydrogels produced from 1 g of 7H4 NaCMC and either 0.01 or 0.001 g of PEGDE$_{500}$ without heat treatment and both with and without catalyst.

FIGS. 5 and 6 are graphs of MUR vs. time and simulated physiological conditions for hydrogels produced from 7H3 NaCMC or 7H4 NaCMC and PEGDE$_{500}$ at a PEGDE$_{500}$/NaCMC weight ratio of either 0.01 or 0.001 prepared without heat treatment and both with and without catalyst (FIG. 5: reactions 5, 8, 13 and 14; FIG. 6: reactions 21, 22, 27 and 28). The results show that the hydrogels produced in the absence of catalyst have significant MUR under gastric and intestinal conditions, but dissolve under colonic conditions. In contrast, hydrogels produced in the presence of the basic catalyst dissolve under gastric conditions.

Figure 7:
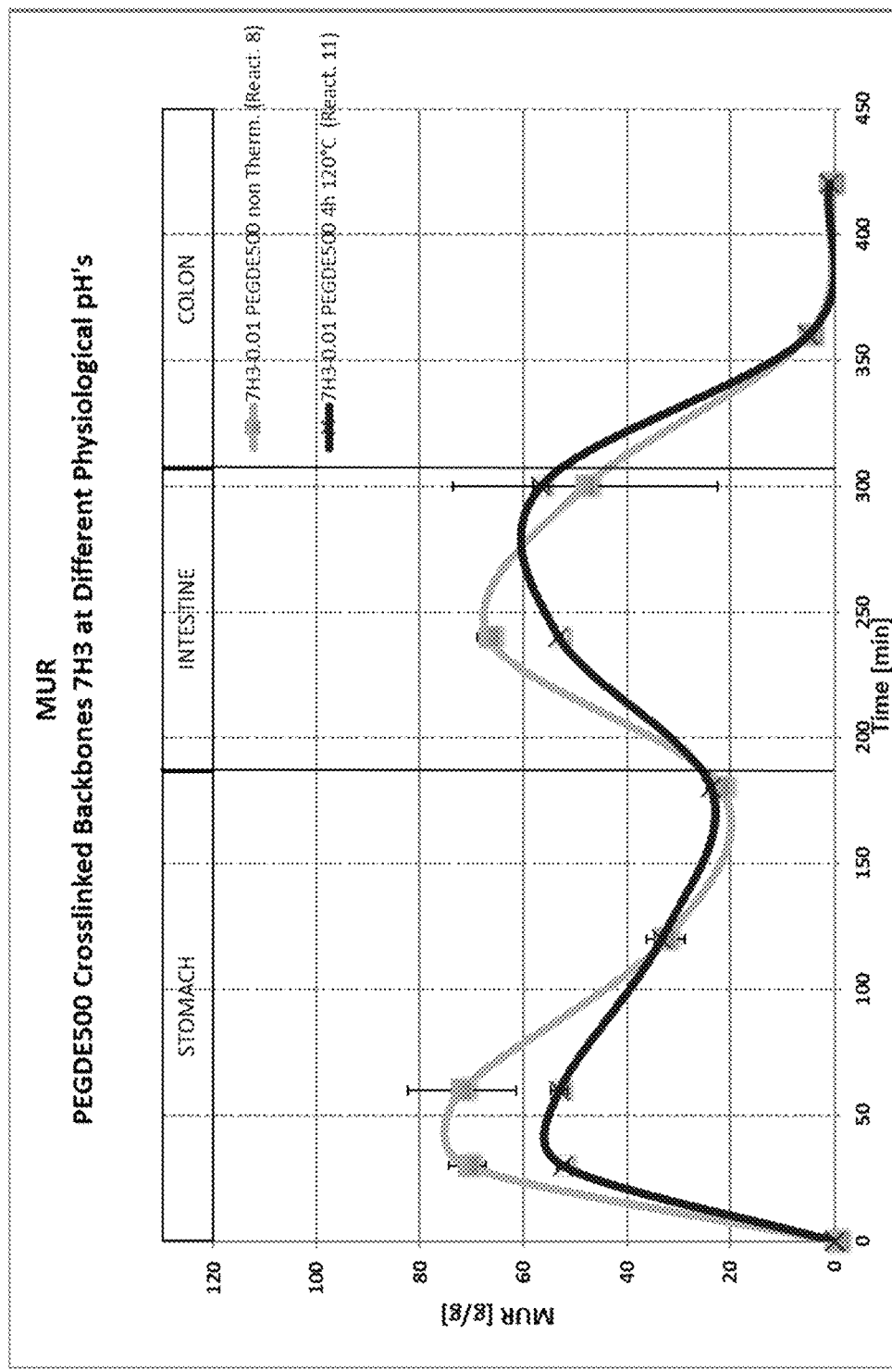
FIG. 7 is a graph of MUR vs. time and simulated physiological conditions for hydrogels produced from 1 g of 7H3 NaCMC and 0.01 g of PEGDE$_{500}$ in the absence of catalyst and both with and without heat treatment.

FIG. 7 is a graph of MUR vs. time and simulated physiological conditions for hydrogels produced from 7H3 NaCMC and PEGDE$_{500}$ at a PEGDE$_{500}$/NaCMC weight ratio of 0.01 in the absence of catalyst and both with and without heat treatment (reactions 8 and 11). The results show that the hydrogel produced without heat treatment has a greater MUR under both gastric and intestinal conditions compared to the heat-treated hydrogel. Both hydrogels dissolve under colonic conditions.

Figure 8:
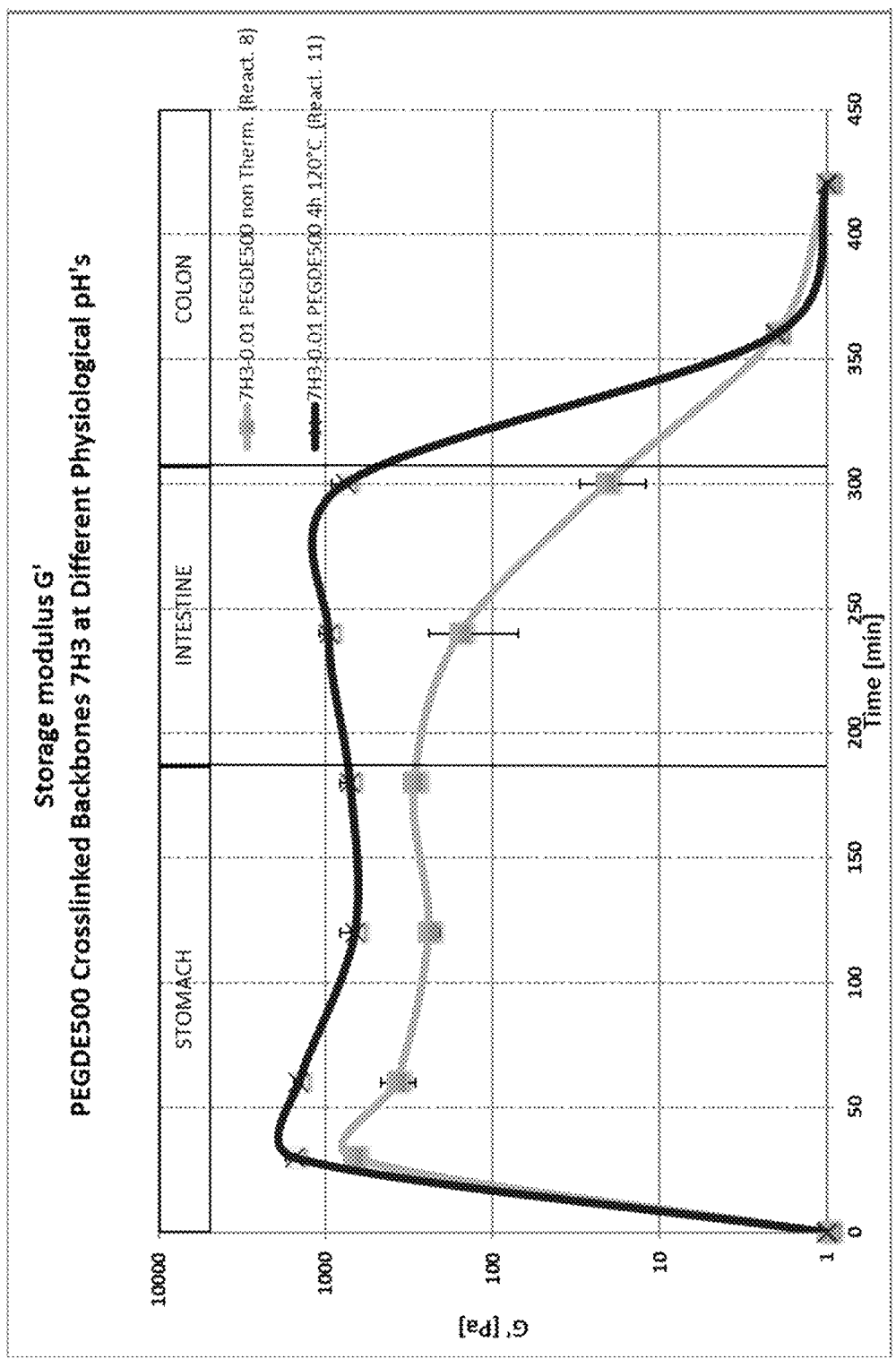
FIG. 8 is graph of G' vs. time and simulated physiological conditions for the two hydrogels presented in FIG. 7.

FIG. 8 is graph of G' vs. time and simulated physiological conditions for the two hydrogels presented in FIG. 7. The results show that at all times prior to dissolution, the G' of the heat treated hydrogel is significantly greater than that of the hydrogel which was not heat treated.

Figure 9:
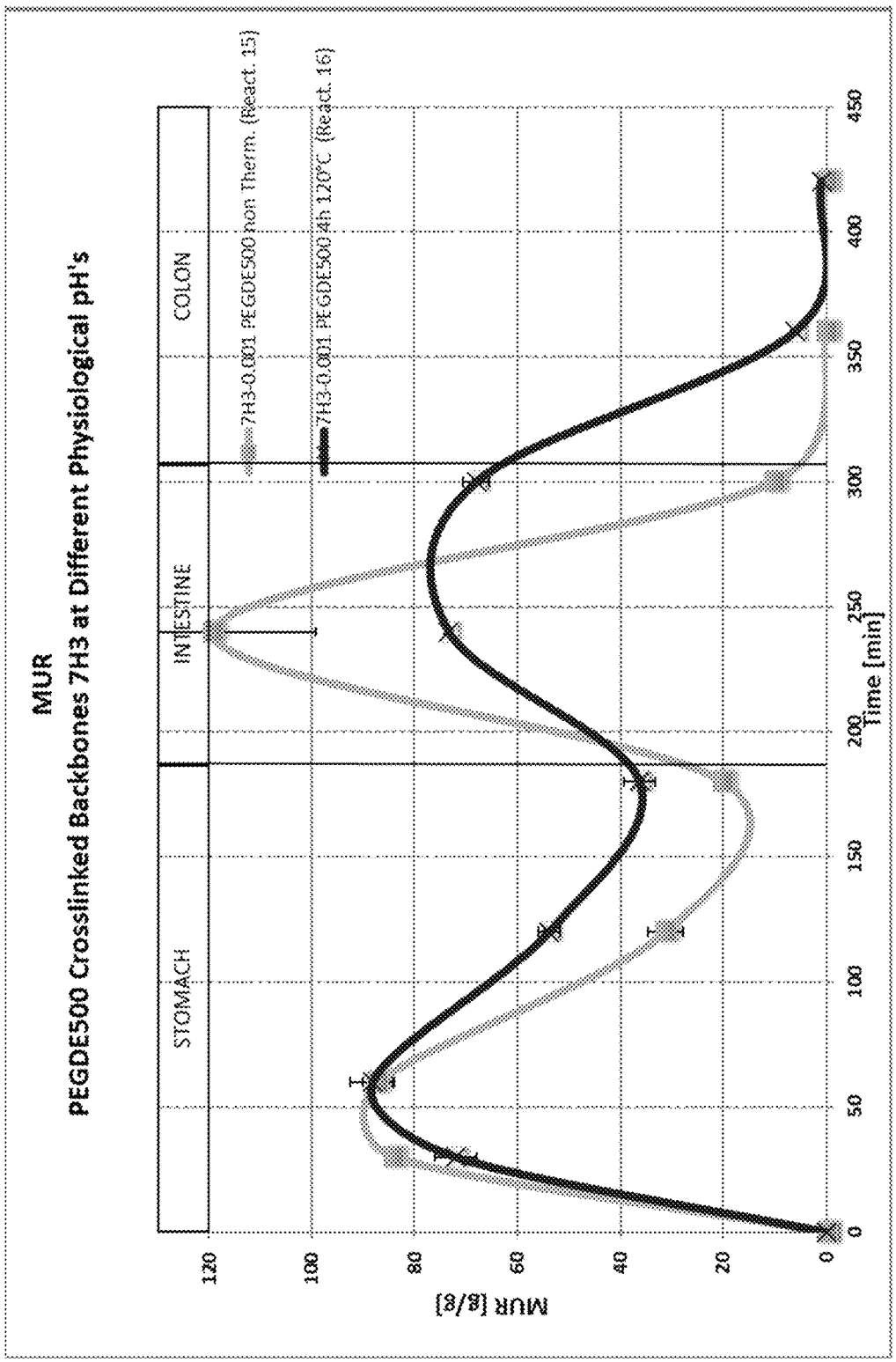
FIG. 9 is a graph of MUR vs. time and simulated physiological conditions for hydrogels produced from 1 g of 7H3 NaCMC and 0.001 g of PEGDE$_{500}$ in the absence of catalyst and both with and without heat treatment.

FIG. 9 is a graph of MUR vs. time and simulated physiological conditions for hydrogels produced from 7H3 NaCMC and PEGDE$_{500}$ at a PEGDE$_{500}$/NaCMC weight ratio of 0.001 in the absence of catalyst and both and without heat treatment (reactions 15 and 16). The results show that both hydrogels have similar MUR under gastric conditions, but the hydrogel produced without heat treatment has a greater MUR under intestinal conditions. Both hydrogels dissolve under colonic conditions.

Figure 10:
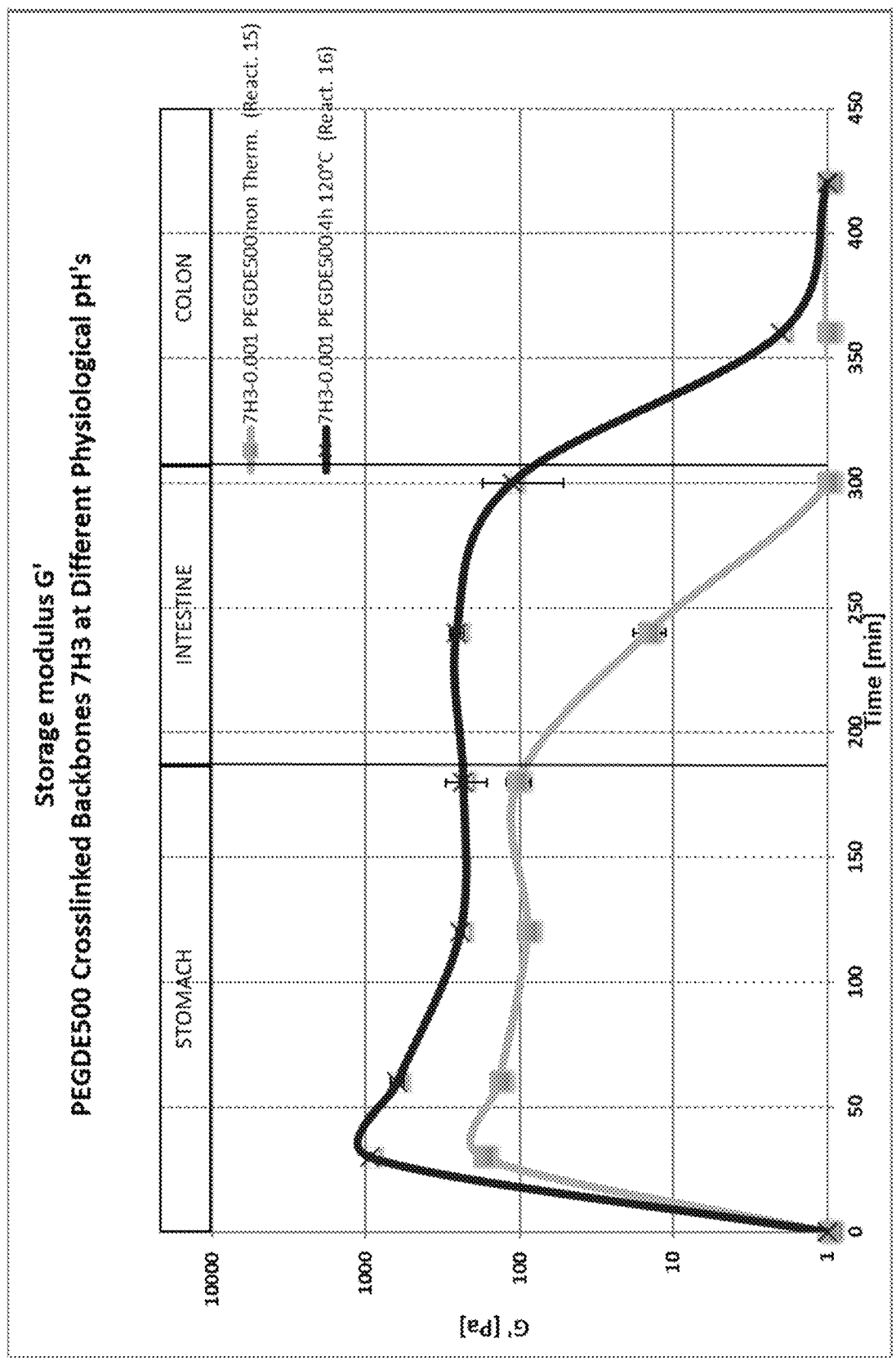
FIG. 10 is graph of G' vs. time and simulated physiological conditions for the two hydrogels presented in FIG. 9.

FIG. 10 is graph of G' vs. time and simulated physiological conditions for the two hydrogels presented in FIG. 9. The results show that at all times prior to dissolution, the G' of the heat treated hydrogel is significantly greater than that of the hydrogel which was not heat treated.

Figure 11:
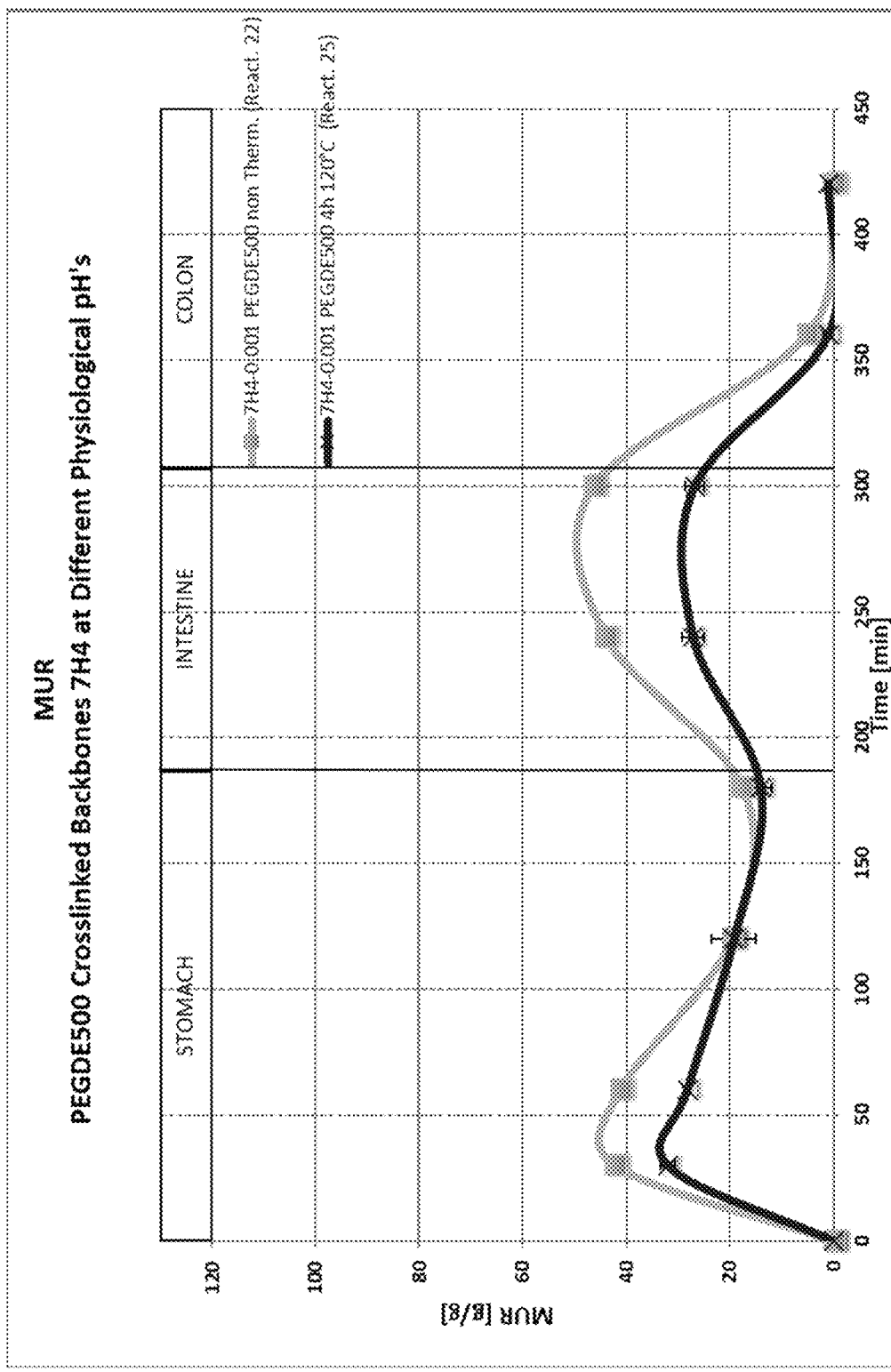
FIG. 11 is a graph of MUR vs. time and simulated physiological conditions for hydrogels produced from 1 g of 7H4 NaCMC and 0.001 g of PEGDE$_{500}$ in the absence of catalyst and both with and without heat treatment.

FIG. 11 is a graph of MUR vs. time and simulated physiological conditions for hydrogels produced from 7H4 NaCMC and PEGDE$_{500}$ at a PEGDE$_{500}$/NaCMC weight ratio of 0.001 in the absence of catalyst and both and without heat treatment (reactions 22 and 25). The results show that the hydrogel produced without heat treatment has a greater MUR under gastric and intestinal conditions compared to the heat treated hydrogel. Both hydrogels dissolve under colonic conditions.

Figure 12:
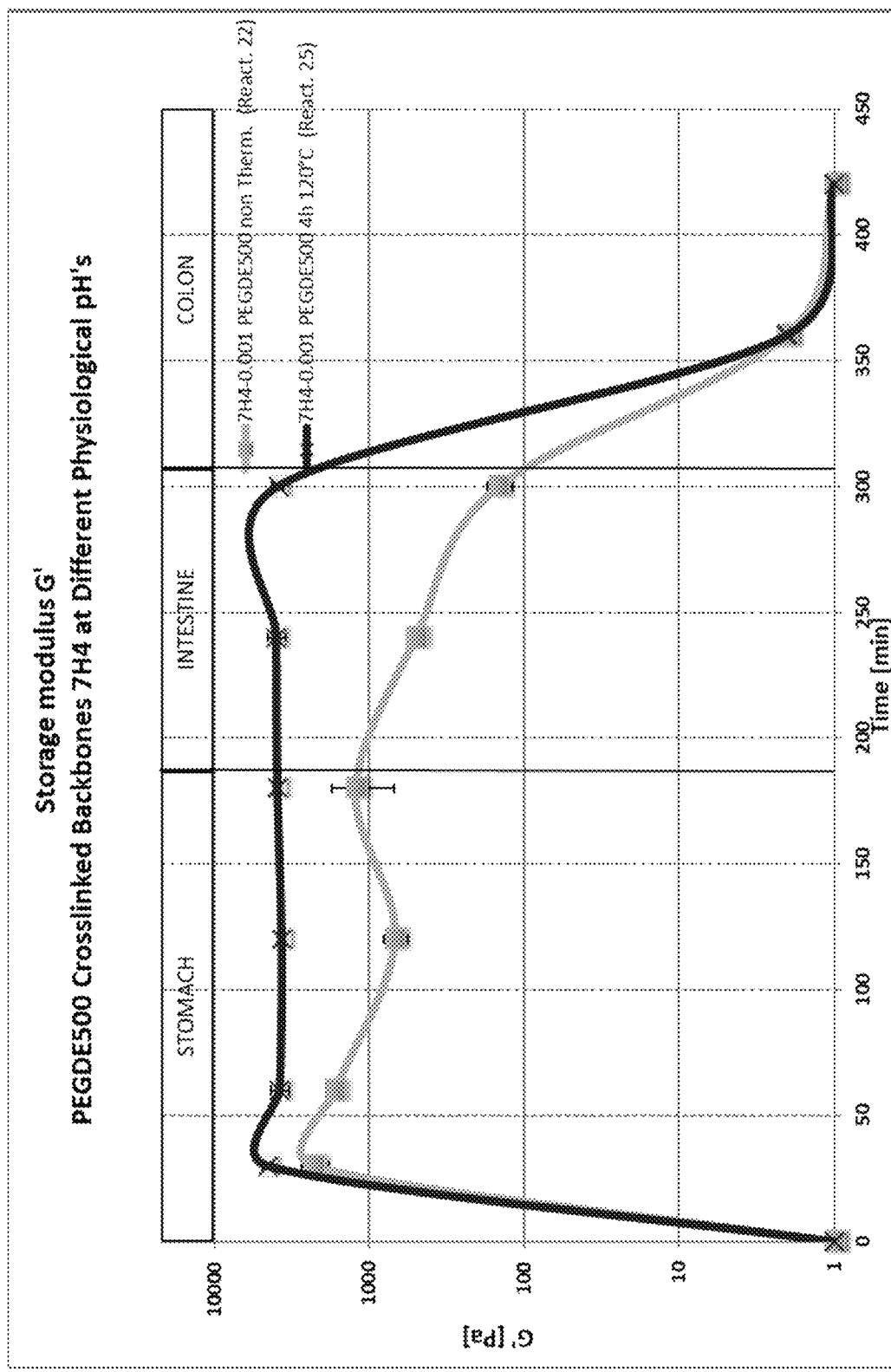
FIG. 12 is graph of G' vs. time and simulated physiological conditions for the two hydrogels presented in FIG. 11.

FIG. 12 is graph of G' vs. time and simulated physiological conditions for the two hydrogels presented in FIG. 11. The results show that at all times prior to dissolution, the G' of the heat treated hydrogel is significantly greater than that of the hydrogel which was not heat treated.

Figure 13:
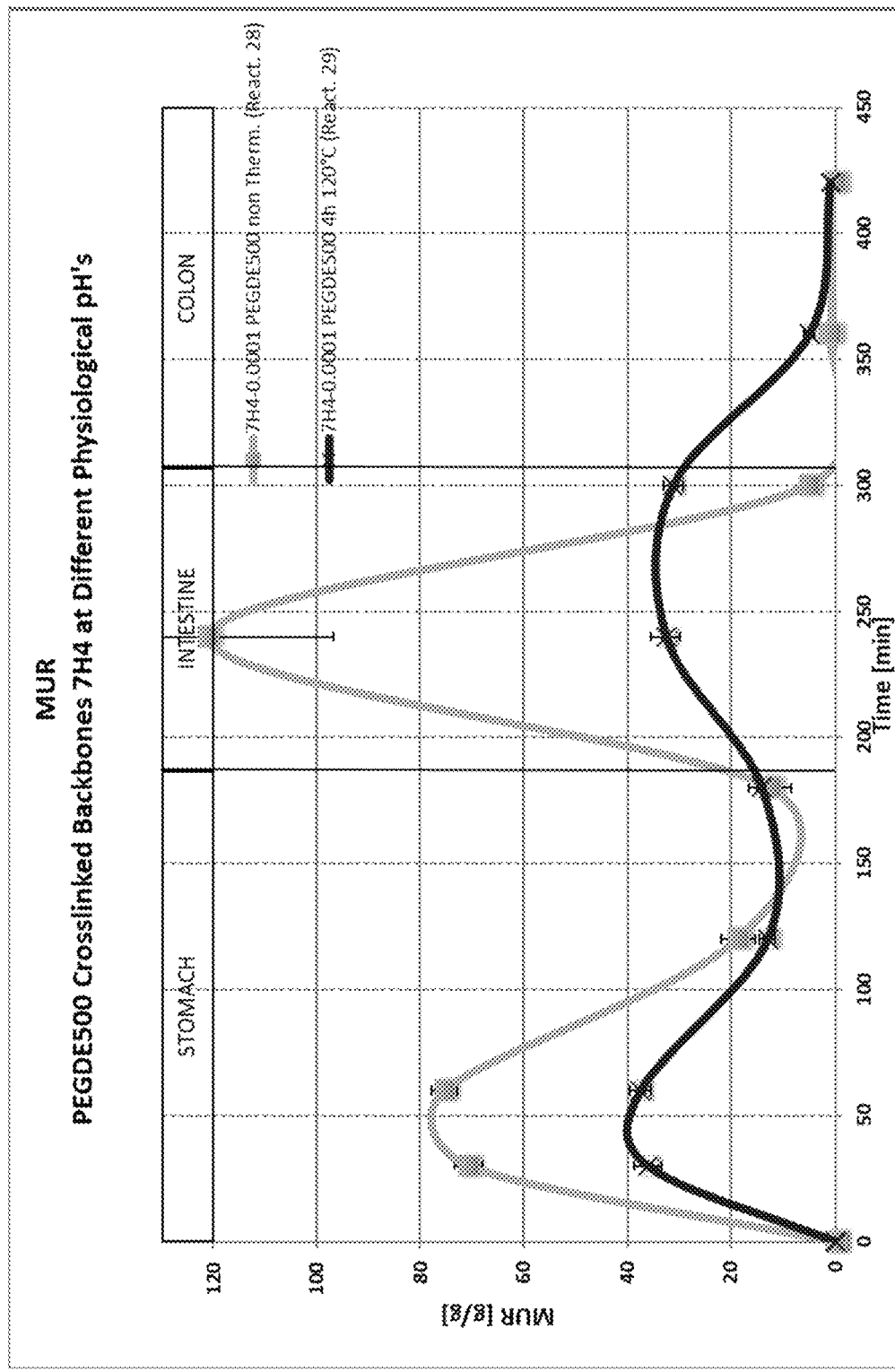
FIG. 13 is a graph of MUR vs. time and simulated physiological conditions for hydrogels produced from 1 g of 7H4 NaCMC and 0.0001 g of PEGDE$_{500}$ in the absence of catalyst and both with and without heat treatment.

FIG. 13 is a graph of MUR vs. time and simulated physiological conditions for hydrogels produced from 7H4 NaCMC and PEGDE$_{500}$ at a PEGDE$_{500}$/NaCMC weight ratio of 0.0001 in the absence of catalyst and both and without heat treatment (reactions 28 and 29). The results show that the hydrogel produced without heat treatment has a greater MUR under gastric and intestinal conditions compared to the heat treated hydrogel. Both hydrogels dissolve under colonic conditions.

Figure 14:
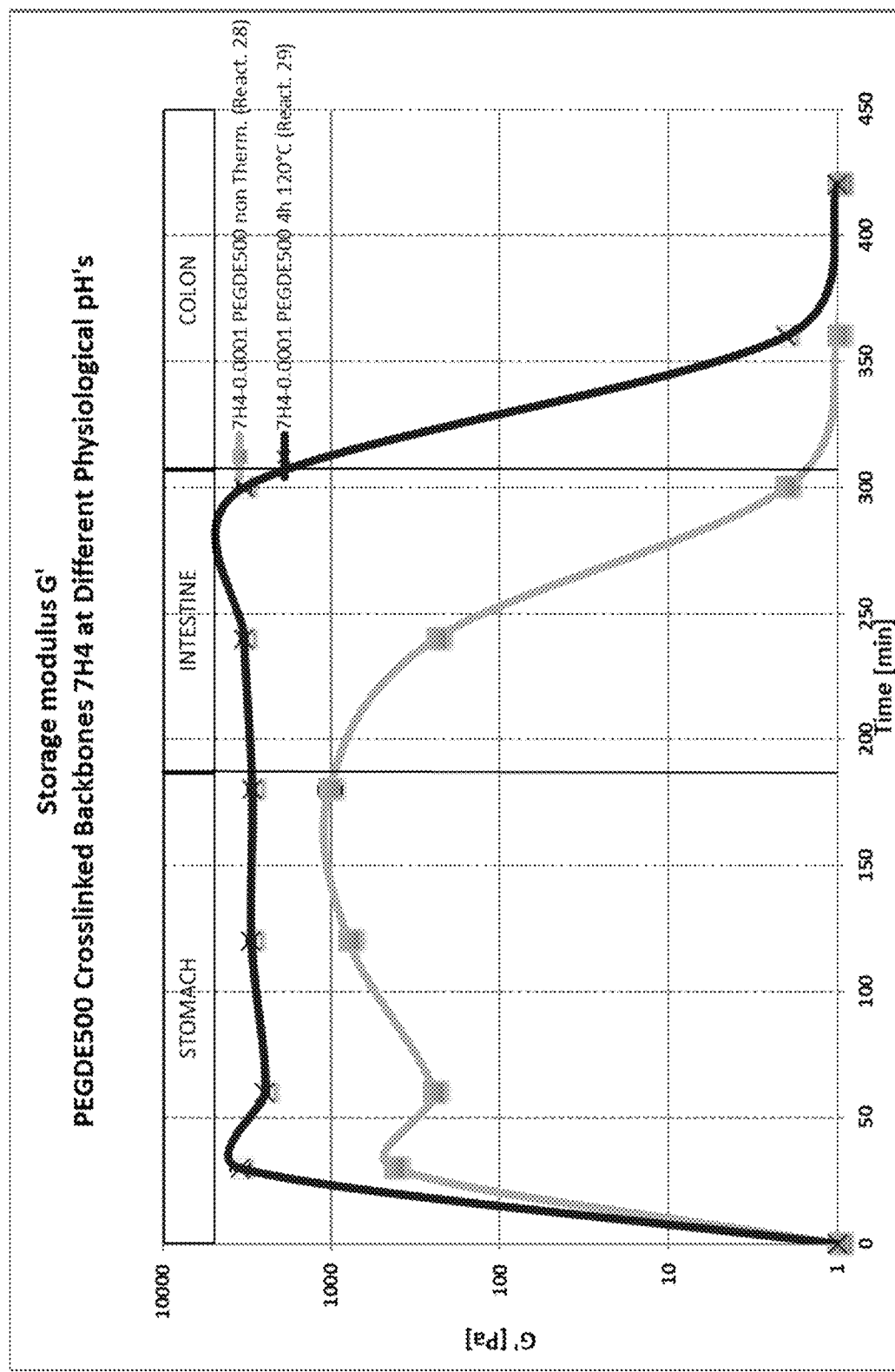
FIG. 14 is graph of G' vs. time and simulated physiological conditions for the two hydrogels presented in FIG. 13.

FIG. 14 is graph of G' vs. time and simulated physiological conditions for the two hydrogels presented in FIG. 13. The results show that at all times prior to dissolution, the G' of the heat treated hydrogel is significantly greater than that of the hydrogel which was not heat treated.

Figure 15:
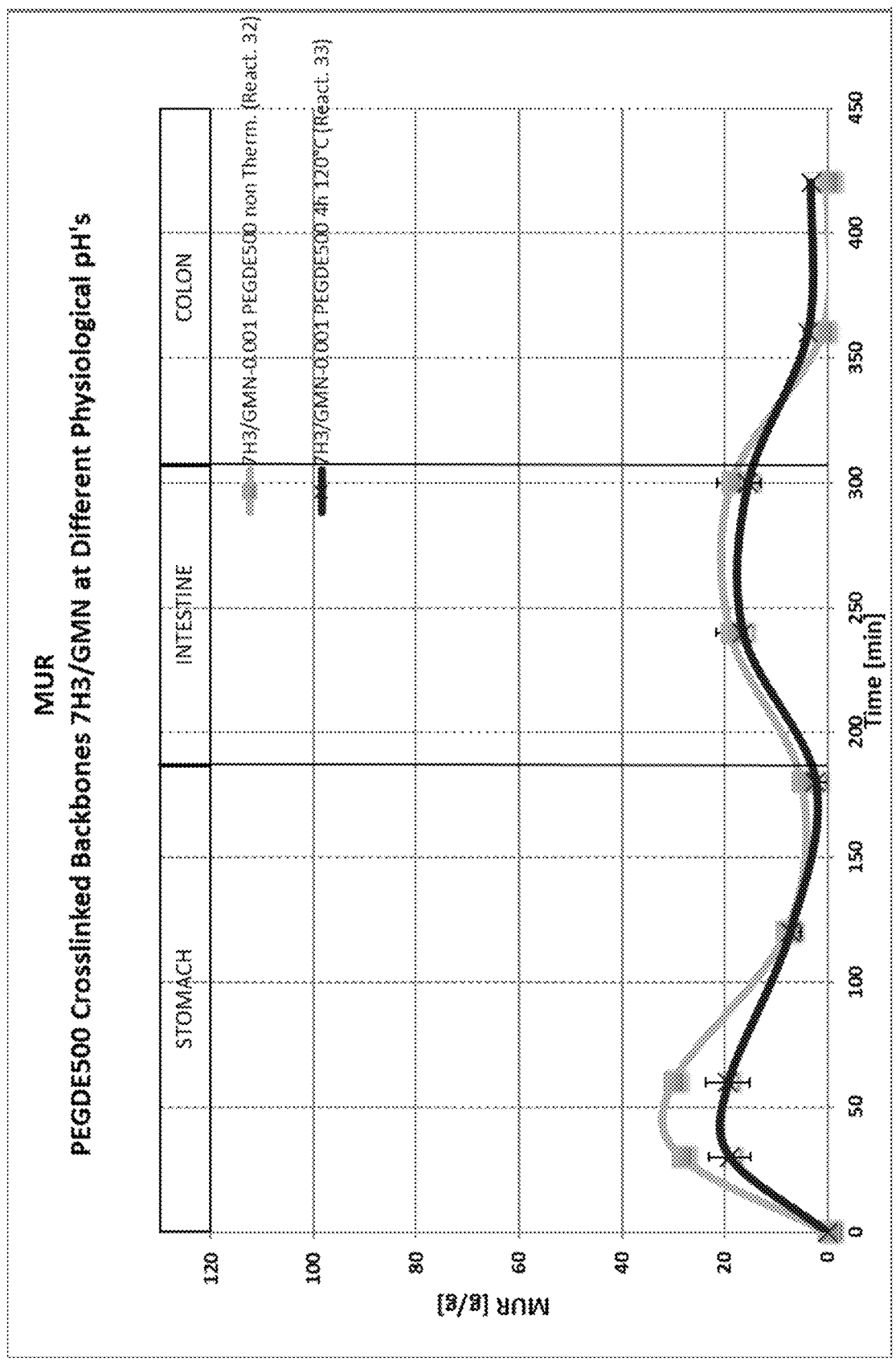
FIG. 15 is a graph of MUR vs. time and simulated physiological conditions for hydrogels produced from 1 g of 7H3 NaCMC/glucomannan (3:1 wt/wt) and 0.01 g of $PEGDE_{500}$ in the absence of catalyst and both and without heat treatment.

FIG. 15 is a graph of MUR vs. time and simulated physiological conditions for hydrogels produced from 7H3 NaCMC/glucomannan (3:1 wt/wt) and PEGDE$_{500}$ at a PEGDE$_{500}$/polymer weight ratio of 0.001 in the absence of catalyst and both and without heat treatment (reactions 32 and 33). The results show that the hydrogel produced without heat treatment has a greater MUR under gastric and intestinal conditions compared to the heat treated hydrogel. Both hydrogels dissolved under colonic conditions.

Figure 16:
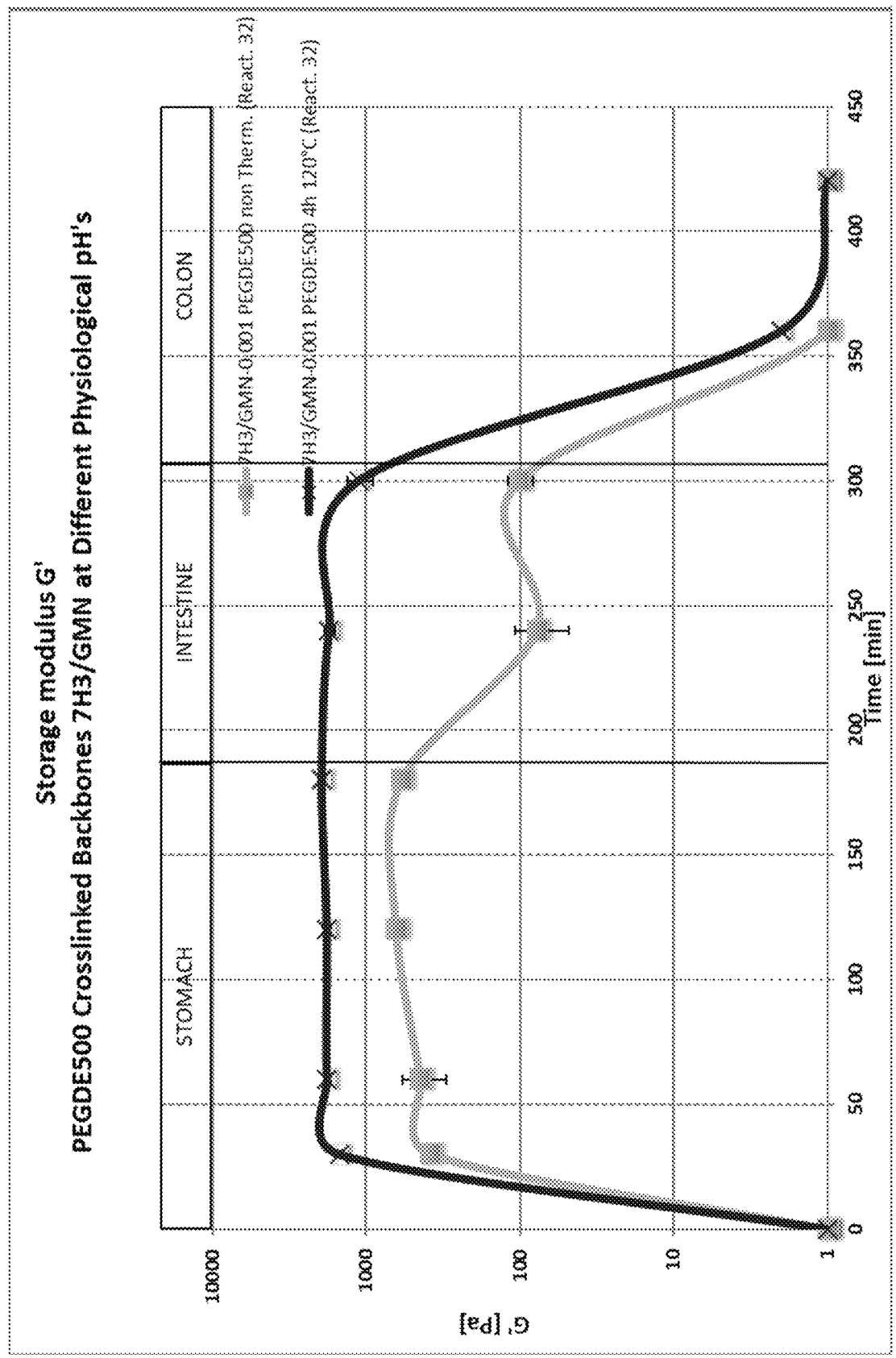
FIG. 16 is graph of G' vs. time and simulated physiological conditions for the two hydrogels presented in FIG. 15.

FIG. 16 is graph of G' vs. time and simulated physiological conditions for the two hydrogels presented in FIG. 15. The results show that at all times prior to dissolution, the G' of the heat treated hydrogel is significantly greater than that of the hydrogel which was not heat treated.

Figure 17:
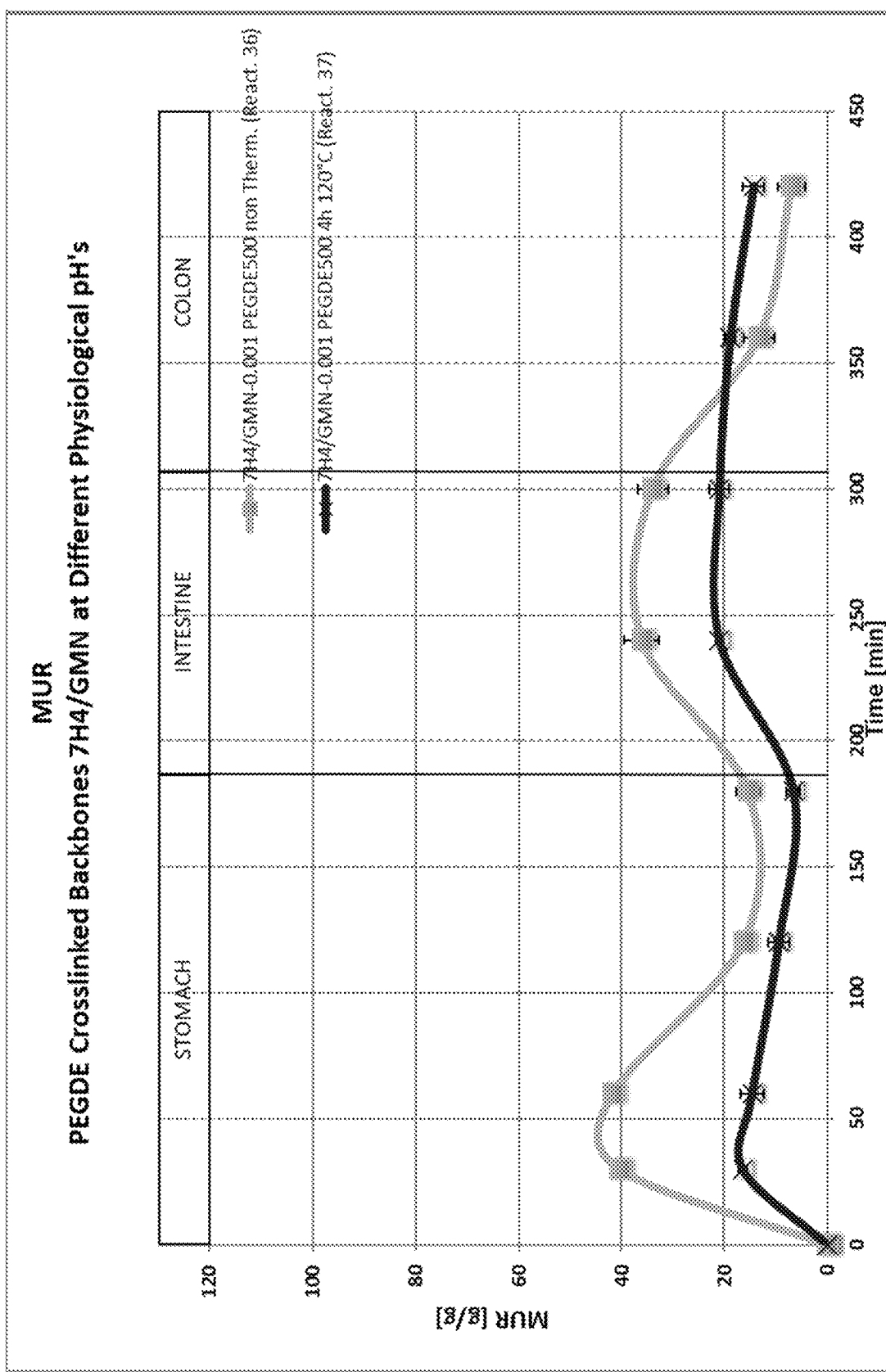
FIG. 17 is a graph of MUR vs. time and simulated physiological conditions for hydrogels produced from 1 g of 7H4 NaCMC/glucomannan (3:1 wt/wt) and 0.001 g of $PEGDE_{500}$ in the absence of catalyst and both and without heat treatment.

FIG. 17 is a graph of MUR vs. time and simulated physiological conditions for the hydrogel produced from 1 g of 7H4 NaCMC/glucomannan (3:1 wt/wt) and PEGDE$_{500}$ at a PEGDE$_{500}$/polymer weight ratio of 0.001 in the absence of catalyst and both and without heat treatment in the absence of catalyst and with and without heat treatment (reactions 36 and 37). The results show a significantly greater MUR for the hydrogel produced without heat treatment.

Figure 18:
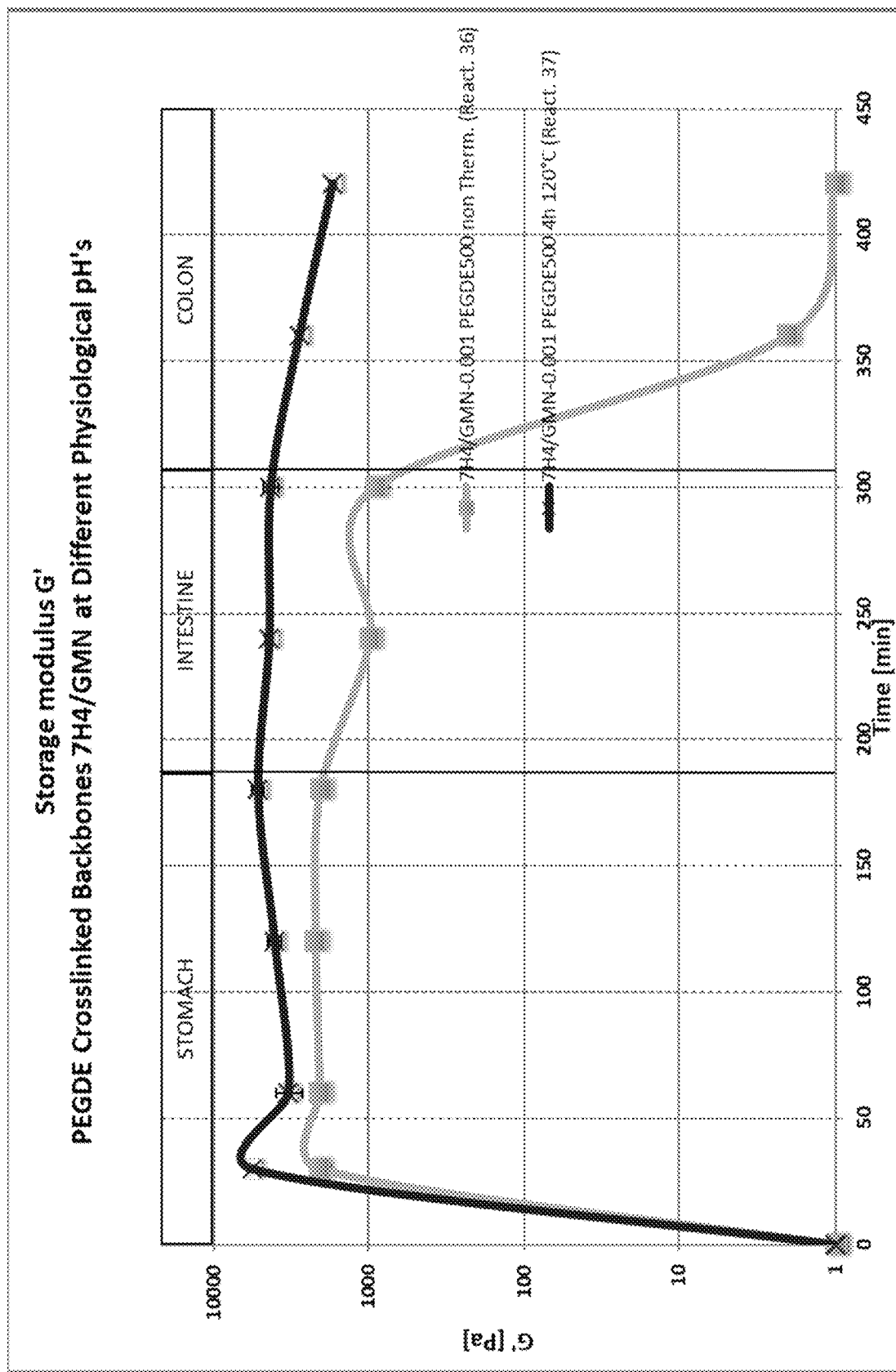
FIG. 18 is graph of G' vs. time and simulated physiological conditions for the two hydrogels presented in FIG. 17.

FIG. 18 is graph of G' vs. time and simulated physiological conditions for the hydrogel presented in FIG. 17. The results show a significantly greater G' for the hydrogel produced with heat treatment.

Figure 19:
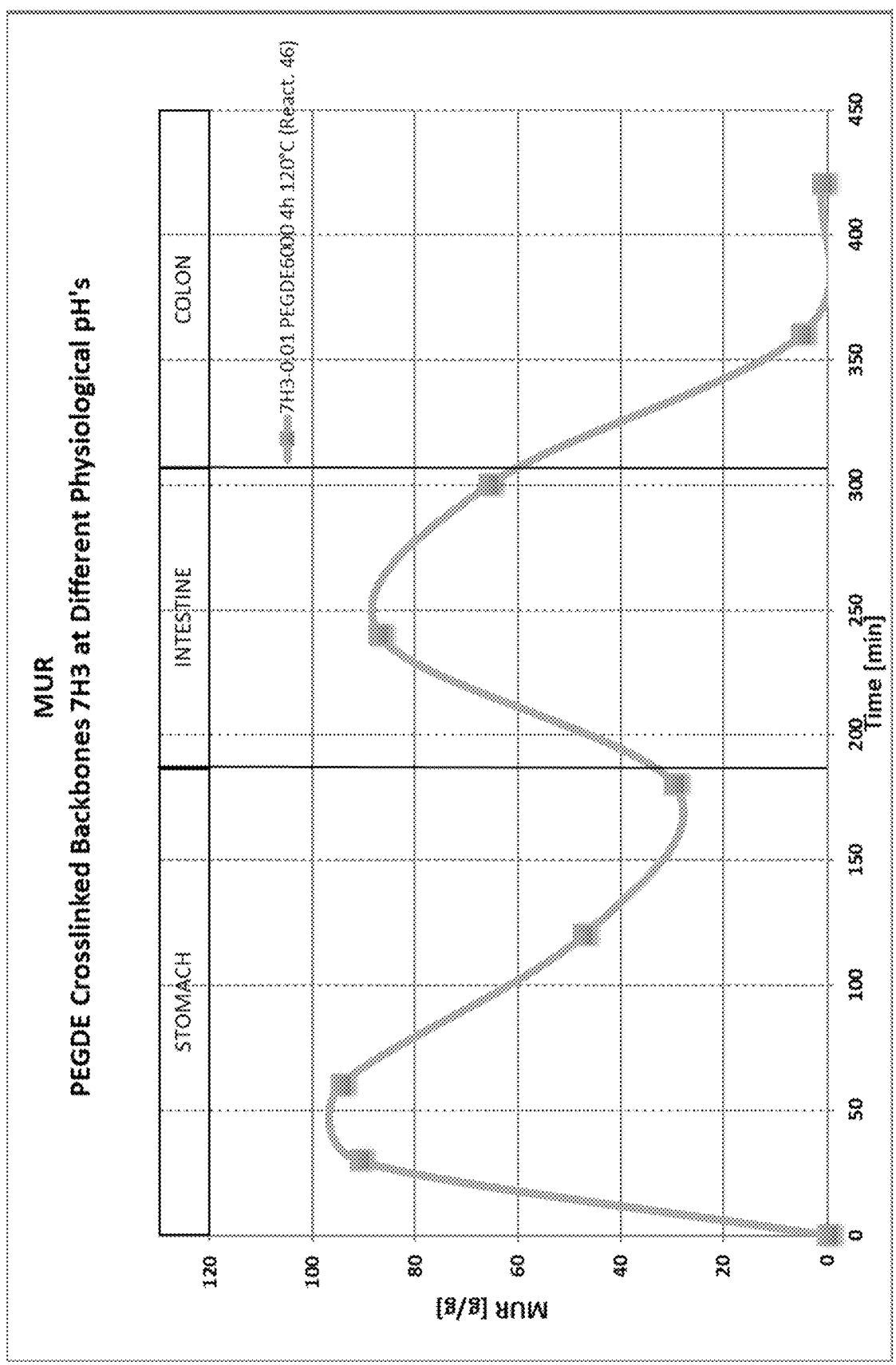
FIG. 19 is a graph of MUR vs. time and simulated physiological conditions for a hydrogel produced from 1 g of 7H3 NaCMC and 0.01 g of $PEGDE_{6000}$ in the absence of catalyst and with heat treatment.

FIG. 19 is a graph of MUR vs. time and simulated physiological conditions for the hydrogel produced from 1 g of 7H3 NaCMC and 0.01 g of PEGDE$_{6000}$ in the absence of catalyst and with heat treatment (reaction 46).

Figure 20:
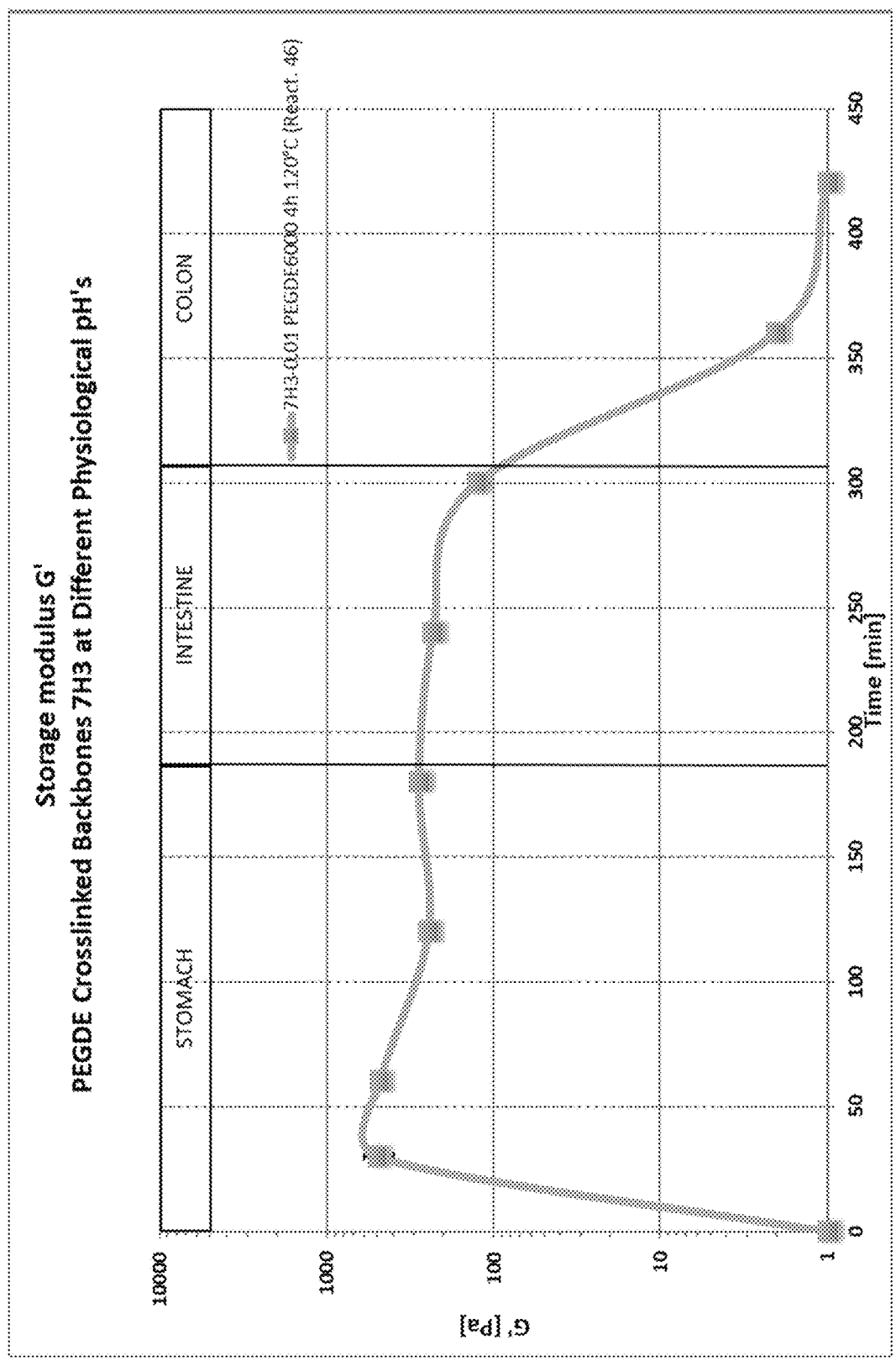
FIG. 20 is graph of G' vs. time and simulated physiological conditions for the hydrogel presented in FIG. 19.

FIG. 20 is a graph of G' vs. time and simulated physiological conditions for the hydrogel presented in FIG. 19.

Figure 21:
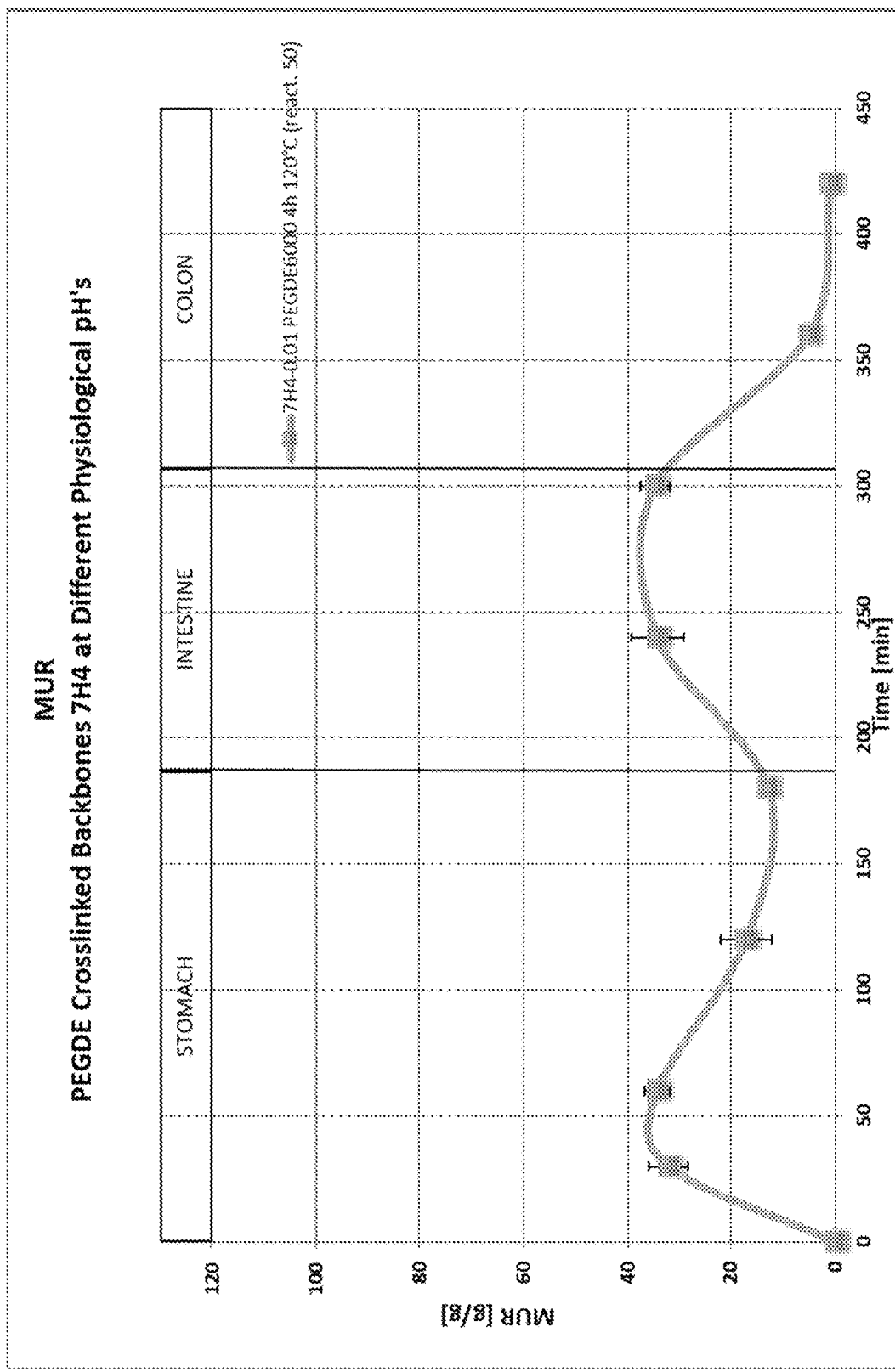
FIG. 21 is a graph of MUR vs. time and simulated physiological conditions for a hydrogel produced from 1 g of 7H4 NaCMC and 0.01 g of $PEGDE_{6000}$ in the absence of catalyst and with heat treatment.

FIG. 21 is a graph of MUR vs. time and simulated physiological conditions for hydrogel produced from 1 g of 7H4 NaCMC and 0.01 g of PEGDE$_{6000}$ in the absence of catalyst and with heat treatment (reaction 50). The MUR for this hydrogel is significantly less than that of the hydrogel of FIG. 19.

Figure 22:
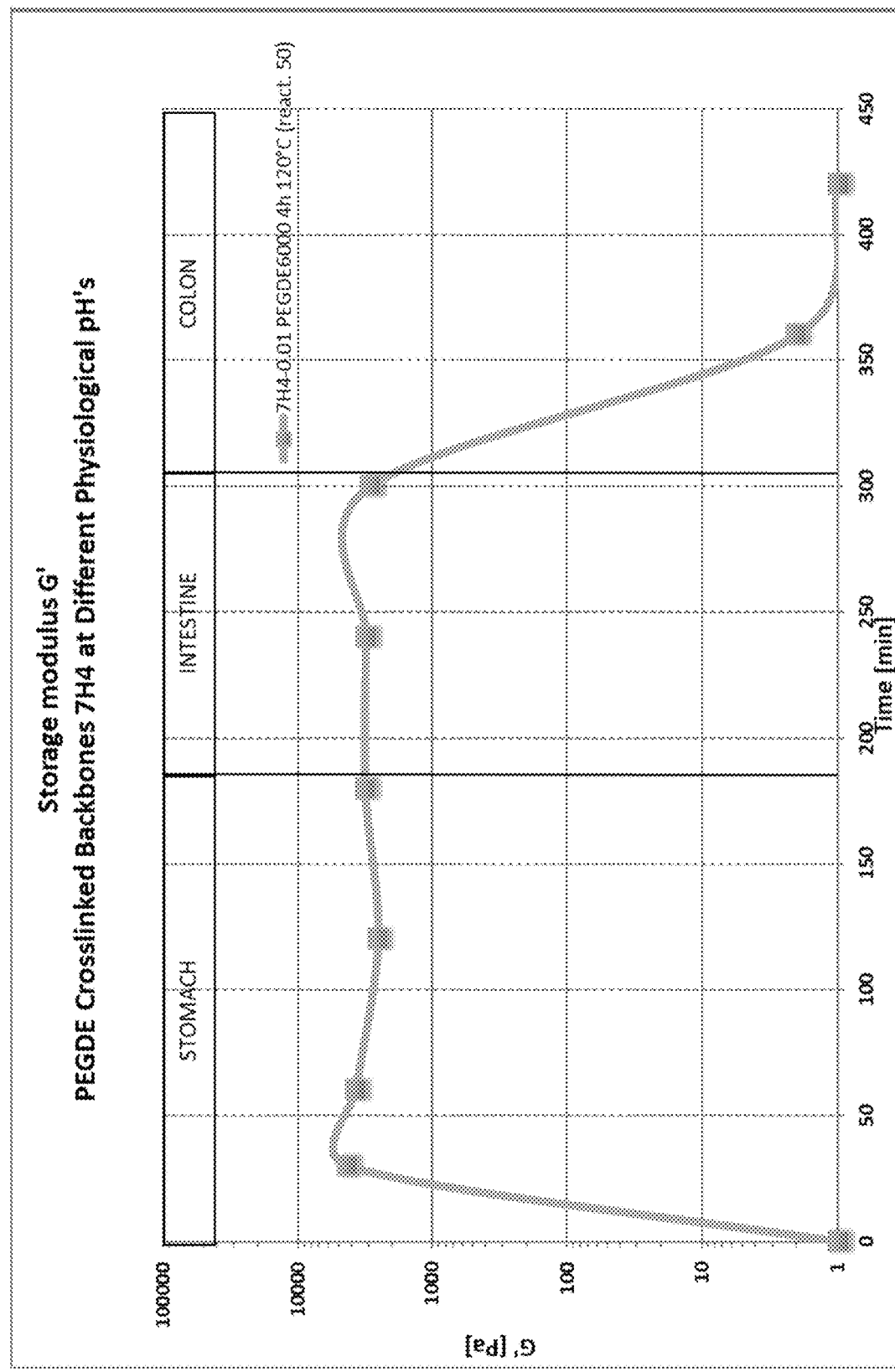
FIG. 22 is graph of G' vs. time and simulated physiological conditions for the hydrogel presented in FIG. 21.

FIG. 22 is a graph of G' vs. time and simulated physiological conditions for the hydrogel presented in FIG. 21.

Figure 23:
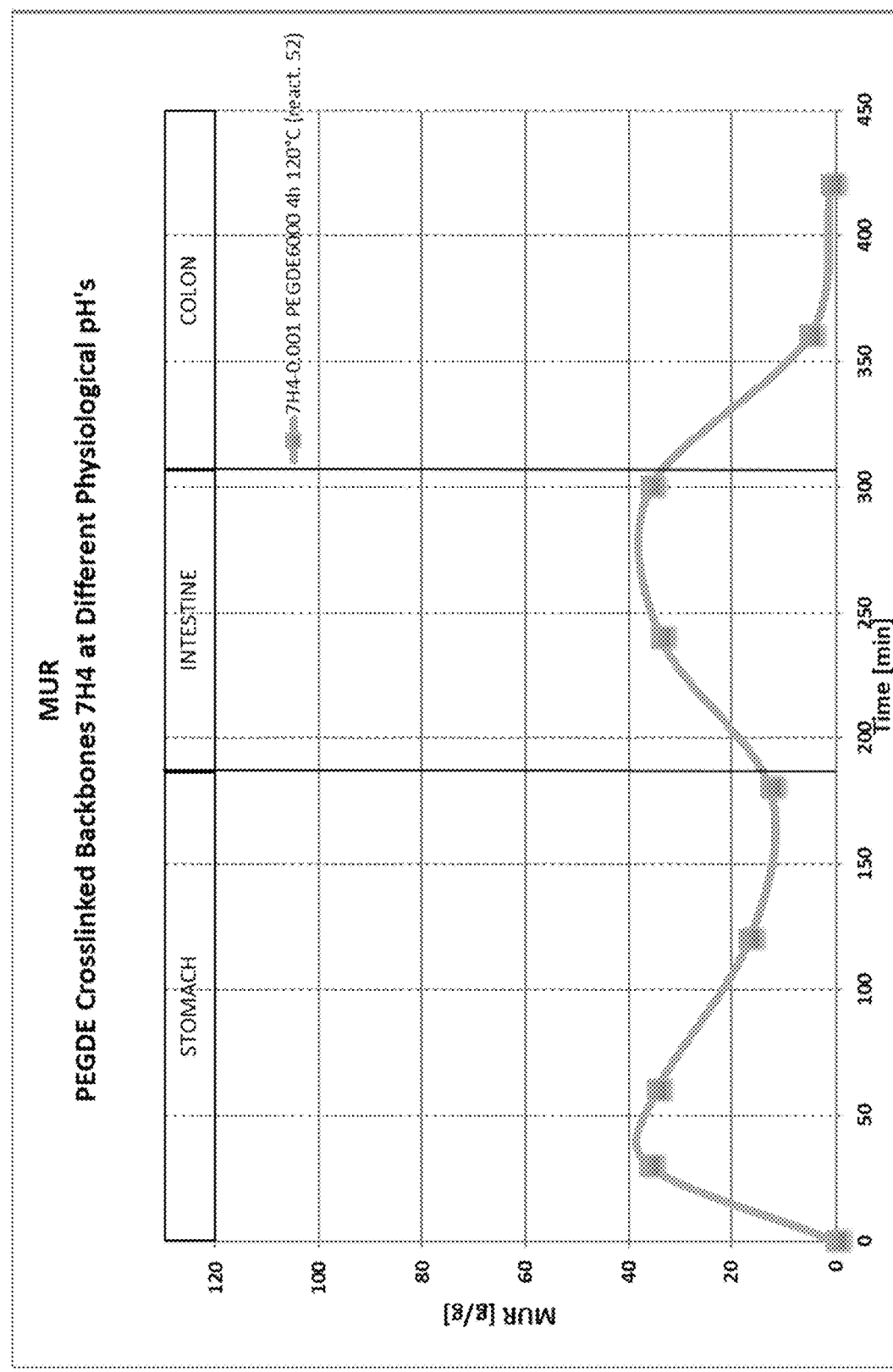
FIG. 23 is a graph of MUR vs. time and simulated physiological conditions for a hydrogel produced from 1 g of 7H4 NaCMC and 0.001 g of $PEGDE_{6000}$ in the absence of catalyst and with heat treatment.

FIG. 23 is a graph of MUR vs. time and simulated physiological conditions for hydrogel produced from 1 g of 7H4 NaCMC and 0.001 g of PEGDE$_{6000}$ in the absence of catalyst and with heat treatment (reaction 52).

Figure 24:
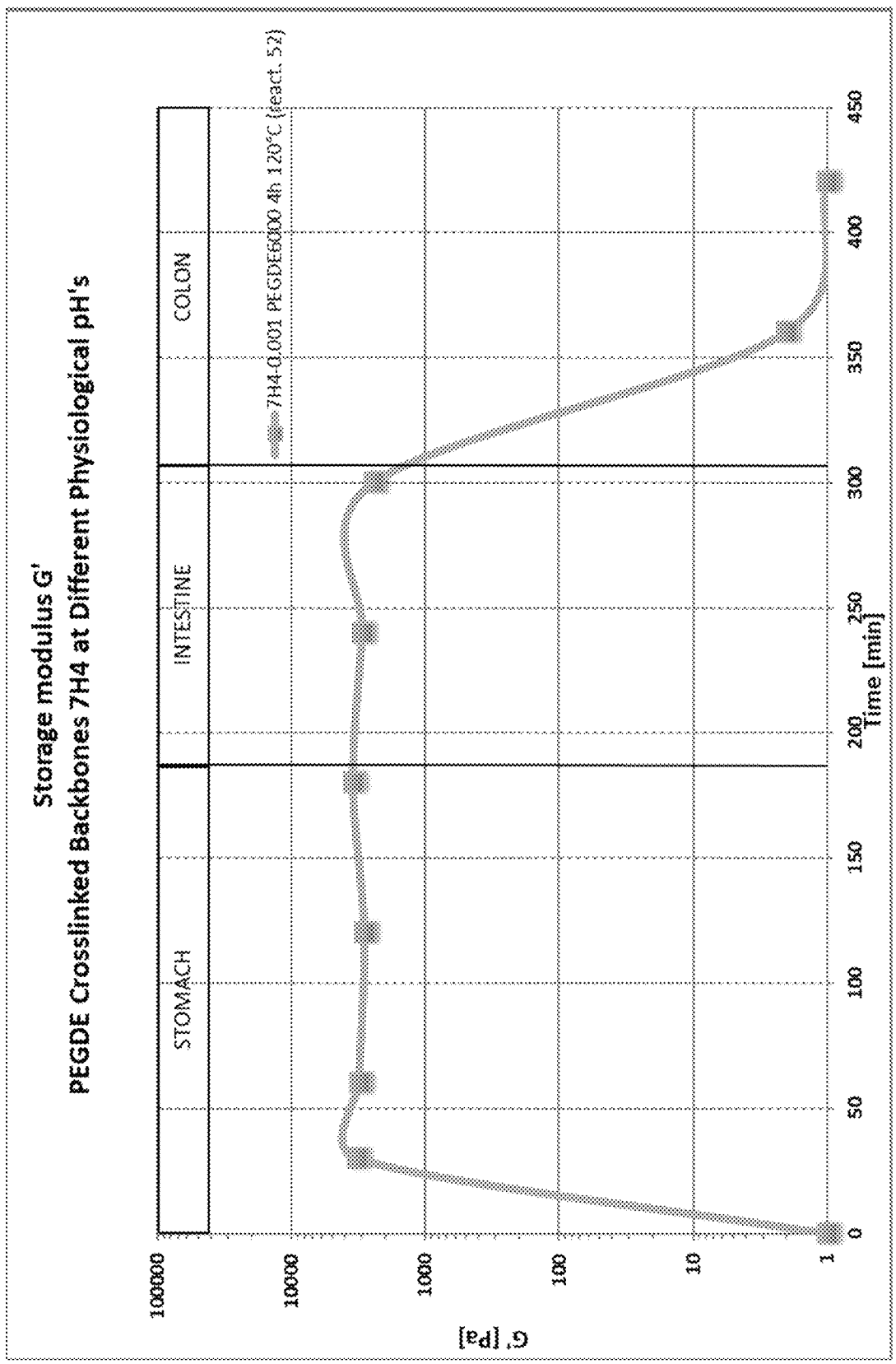
FIG. 24 is graph of G' vs. time and simulated physiological conditions for the hydrogel presented in FIG. 23.

FIG. 24 is a graph of G' vs. time and simulated physiological conditions for the hydrogel presented in FIG. 23.

The results show that hydrogels produced by crosslinking carboxymethylcellulose with relatively low levels of PEGDE$_{500}$ in the presence of basic catalyst lose their structural integrity and dissolve under simulated gastric conditions. In contrast, hydrogels prepared in the absence of catalyst, whether or not heat treated, remained intact under both simulated gastric and intestinal conditions and dissolved under simulated colonic conditions. In addition, heat treating the hydrogel decreases MUR under simulated gastric and intestinal conditions, but increased G' under these conditions.

While this invention has been particularly shown and described with references to preferred embodiments thereof, it will be understood by those skilled in the art that various changes in form and details may be made therein without departing from the scope of the invention encompassed by the appended claims.

We claim:

1. A method of producing a polymer hydrogel, comprising the steps of (a) preparing an aqueous solution of at least one water soluble polysaccharide and a bifunctional PEG; (b) evaporating the water from the solution to produce a solid residue; and (c) heating the solid residue to a temperature of at least 100° C., thereby producing the polymer hydrogel, provided that (i) the solution of step (a) does not comprise an acid or base catalyst and (ii) the molar ratio of polysaccharide monomeric units to bifunctional PEG is at least 200.

2. The method of claim 1, wherein the total concentration of water soluble polysaccharide in the aqueous solution of step (a) is at least 0.5% by weight relative to water.

3. The method of claim 2, wherein the total concentration of water soluble polysaccharide in the aqueous solution of step (a) is 4-10% by weight relative to water.

4. The method of claim 1, wherein in step (c) the solid residue is heated for at least 1 hour.

5. The method of claim 1, wherein the solid residue of step (b) is comminuted prior to step (c).

6. The method of claim 1, wherein the at least one water soluble polysaccharide is ionic.

7. The method of claim 6, wherein the at least one water soluble polysaccharide is carboxymethylcellulose.

8. The method of claim 1, where the aqueous solution comprises carboxymethylcellulose and glucomannan.

9. The method of claim 1, wherein the bifunctional PEG is PEGDE.

10. The method of claim 7, wherein the carboxymethylcellulose has a viscosity in a 1% (wt/wt) aqueous solution at 25° C. of from 500 to 1000 cps.

11. The method of claim 7, wherein the carboxymethylcellulose has a viscosity in a 1% (wt/wt) aqueous solution at 25° C. of at least 6000 cps.

* * * * *